US011890384B2

(12) United States Patent
Clare et al.

(10) Patent No.: US 11,890,384 B2
(45) Date of Patent: Feb. 6, 2024

(54) CHITOSAN SUPERFINE FIBER SYSTEMS

(71) Applicant: Tricol Biomedical, Inc., Portland, OR (US)

(72) Inventors: Brian Clare, Portland, OR (US); Radim Dvořák, Popůvky (CZ); Simon McCarthy, Portland, OR (US); Jiri Machát, Brno (CZ)

(73) Assignee: Tricol Biomedical, Inc., Portland, OR (US)

(*) Notice: Subject to any disclaimer, the term of this patent is extended or adjusted under 35 U.S.C. 154(b) by 0 days.

(21) Appl. No.: 15/431,168

(22) Filed: Feb. 13, 2017

(65) Prior Publication Data

US 2017/0232134 A1    Aug. 17, 2017

Related U.S. Application Data

(60) Provisional application No. 62/294,994, filed on Feb. 12, 2016.

(51) Int. Cl.
| | |
|---|---|
| *A61L 15/28* | (2006.01) |
| *A61L 15/42* | (2006.01) |
| *D01D 5/18* | (2006.01) |
| *A61L 27/50* | (2006.01) |
| *A61L 27/56* | (2006.01) |
| *A61L 24/08* | (2006.01) |
| *A61L 27/20* | (2006.01) |
| *A61L 24/00* | (2006.01) |
| *D01F 9/00* | (2006.01) |
| *D01D 5/08* | (2006.01) |
| *D01D 5/084* | (2006.01) |
| *D01F 1/02* | (2006.01) |
| *D01D 10/02* | (2006.01) |
| *D01D 1/02* | (2006.01) |

(52) U.S. Cl.
CPC ............ *A61L 15/28* (2013.01); *A61L 15/425* (2013.01); *A61L 24/0036* (2013.01); *A61L 24/08* (2013.01); *A61L 27/20* (2013.01); *A61L 27/50* (2013.01); *A61L 27/56* (2013.01); *D01D 5/08* (2013.01); *D01D 5/084* (2013.01); *D01D 5/18* (2013.01); *D01F 9/00* (2013.01); A61L 2400/04 (2013.01); A61L 2430/00 (2013.01); *D01D 1/02* (2013.01); *D01D 10/02* (2013.01); *D01F 1/02* (2013.01)

(58) Field of Classification Search
None
See application file for complete search history.

(56) References Cited

U.S. PATENT DOCUMENTS

| | | |
|---|---|---|
| 692,631 A | 2/1902 | Cooley |
| 705,691 A | 7/1902 | Morton |
| 1,975,504 A | 10/1934 | Formhals |
| 2,077,373 A | 4/1937 | Formhals |
| 2,116,942 A | 5/1938 | Formhals |
| 2,123,992 A | 7/1938 | Formhals |
| 2,109,333 A | 12/1938 | Formhals |
| 2,158,415 A | 5/1939 | Formhals |
| 2,158,416 A | 5/1939 | Formhals |
| 2,160,962 A | 6/1939 | Formhals |
| 2,187,306 A | 1/1940 | Formhals |
| 2,323,025 A | 6/1943 | Formhals |
| 2,349,950 A | 5/1944 | Formhals |
| 4,311,570 A | 1/1982 | Cowen et al. |
| 4,790,736 A | 12/1988 | Keuchel |
| 5,169,889 A | 12/1992 | Kauffman et al. |
| 5,460,498 A | 10/1995 | Steel et al. |
| 5,494,616 A | 2/1996 | Voelker et al. |
| 6,106,913 A | 8/2000 | Scardino et al. |
| 6,369,293 B1 | 4/2002 | Reeves et al. |
| 6,713,011 B2 | 3/2004 | Chu et al. |
| 6,753,454 B1 | 6/2004 | Smith et al. |
| 7,134,857 B2 | 11/2006 | Andrady et al. |
| 7,371,403 B2 | 5/2008 | McCarthy et al. |
| 7,585,437 B2 | 9/2009 | Jirsak et al. |
| 7,592,277 B2 | 9/2009 | Andrady et al. |

(Continued)

FOREIGN PATENT DOCUMENTS

| | | |
|---|---|---|
| CN | 1238061 C | 1/2006 |
| CN | 103691005 A | 4/2014 |

(Continued)

OTHER PUBLICATIONS

Sajeev, U. S., et al. "Control of nanostructures in PVA, PVA/chitosan blends and PCL through electrospinning." Bulletin of Materials Science 31.3 (2008): 343-351.*

Kidoaki, Satoru, Il Kuen Kwon, and Takehisa Matsuda. "Mesoscopic spatial designs of nano-and microfiber meshes for tissue-engineering matrix and scaffold based on newly devised multilayering and mixing electrospinning techniques." Biomaterials 26.1 (2005): 37-46. (Year: 2005).*

(Continued)

*Primary Examiner* — Nissa M Westerberg

(74) *Attorney, Agent, or Firm* — Seed IP Law Group LLP

(57) ABSTRACT

The present chitosan-based superfine fiber invention relates to compositions, formulations, and processes that result in numerous significant advantages for the production and use of superfine fiber bioactive matrices in biomedical applications. The present invention relates to superfine, chitosan-based fibers, wherein the chitosan-based fibers have a percentage chitosan content of at least about 20% w/w, and highly conformable and compliant matrices comprising such fibers, processes for their production, and related formulations. The superfine chitosan-based fibers of the invention preferably include microfibers with diameter less than or equal to about 10 microns and micron and submicron fibers that are about 2 microns and less.

24 Claims, 34 Drawing Sheets

(56) References Cited

U.S. PATENT DOCUMENTS

| | | | |
|---|---|---|---|
| 7,897,832 B2 | 3/2011 | McAdams et al. | |
| 8,231,378 B2 | 7/2012 | Lozano et al. | |
| 8,269,058 B2 | 9/2012 | McCarthy et al. | |
| 8,303,874 B2 | 11/2012 | Marshall et al. | |
| 8,445,671 B2 | 5/2013 | Dvořák et al. | |
| 8,647,540 B2 | 2/2014 | Peno et al. | |
| 8,647,541 B2 | 2/2014 | Peno et al. | |
| 8,658,067 B2 | 2/2014 | Peno et al. | |
| 8,709,309 B2 | 4/2014 | Peno et al. | |
| 8,721,319 B2 | 5/2014 | Lozano et al. | |
| 8,741,335 B2 | 6/2014 | McCarthy | |
| 8,777,599 B2 | 7/2014 | Peno et al. | |
| 8,778,240 B2 | 7/2014 | Peno et al. | |
| 8,828,294 B2 | 9/2014 | Lozano et al. | |
| 8,858,845 B2 | 10/2014 | Peno et al. | |
| 8,920,514 B2 | 12/2014 | Gregory et al. | |
| 9,004,918 B2 | 4/2015 | McAdams et al. | |
| 9,132,206 B2 | 9/2015 | McCarthy | |
| 9,163,338 B2 | 10/2015 | Schauer et al. | |
| 9,194,058 B2 | 11/2015 | Sharma et al. | |
| 9,204,957 B2 | 12/2015 | Gregory et al. | |
| 9,205,170 B2 | 12/2015 | Lucchesi et al. | |
| 9,547,011 B2 | 1/2017 | McGrath et al. | |
| 9,846,163 B2 | 12/2017 | McGrath et al. | |
| 9,925,210 B2 | 3/2018 | McCarthy et al. | |
| 9,925,310 B2 | 3/2018 | McGrath et al. | |
| 10,086,105 B2 | 10/2018 | Guo et al. | |
| 10,632,143 B2 | 4/2020 | McCarthy et al. | |
| 10,709,817 B2 | 7/2020 | McGrath et al. | |
| 11,160,901 B2 | 11/2021 | Bush et al. | |
| 11,229,724 B2 | 1/2022 | McGrath et al. | |
| 11,234,998 B2 | 2/2022 | McCarthy et al. | |
| 2005/0255121 A1* | 11/2005 | Campbell | A61K 39/12 514/57 |
| 2007/0083137 A1 | 4/2007 | Hopman et al. | |
| 2009/0269429 A1 | 10/2009 | Lozano et al. | |
| 2011/0111012 A1 | 5/2011 | Pepper et al. | |
| 2014/0046236 A1 | 2/2014 | Filée et al. | |
| 2014/0051316 A1 | 2/2014 | Zhang et al. | |
| 2014/0275291 A1 | 9/2014 | McGrath et al. | |
| 2015/0031261 A1 | 1/2015 | Branham et al. | |
| 2015/0209392 A1 | 7/2015 | Song et al. | |
| 2015/0216894 A1 | 8/2015 | McCarthy et al. | |
| 2021/0052261 A1 | 2/2021 | Perry et al. | |
| 2021/0052766 A1 | 2/2021 | Gannett et al. | |
| 2021/0059867 A1 | 3/2021 | McCarthy et al. | |
| 2021/0059868 A1 | 3/2021 | Gannett et al. | |
| 2021/0060203 A1 | 3/2021 | McCarthy et al. | |

FOREIGN PATENT DOCUMENTS

| | | |
|---|---|---|
| EP | 2 875 834 A1 | 5/2015 |
| WO | 98/00180 A1 | 1/1998 |

OTHER PUBLICATIONS

Neamnark A, Sanchavanakit N, Pavasant P, Rujiravanit R, Supaphol P. In vitro biocompatibility of electrospun hexanoyl chitosan fibrous scaffolds towards human keratinocytes and fibroblasts. European Polymer Journal. Jul. 1, 2008;44(7):2060-7. (Year: 2008).*

Kang YM, Lee BN, Ko JH, Kim GH, Kang KN, Kim DY, Kim JH, Park YH, Chun HJ, Kim CH, Kim MS. In vivo biocompatibility study of electrospun chitosan microfiber for tissue engineering. International journal of molecular sciences. Oct. 2010; 11(10):4140-8. (Year 2010).*

Chen Z, Mo X, He C, Wang H. Intermolecular interactions in electrospun collagen-chitosan complex nanofibers. Carbohydrate polymers. May 16, 2008;72(3):410-8. (Year: 2008).*

Xu et al., "Development of tannic acid/chitosan/pullulan composite nanofibers from aqueous solution for potential applications as wound dressing," *Carbohydrate Polymers* 115:16-24, 2015.

Xu et al., "Large-scale production of ternary composite nanofiber membrane for wound dressing applications," *Journal of Bioactive and Compatible Polymers* 29(6):646-660, 2014.

An et al., "Preparation and antibacterial activity of electrospun chitosan/poly(ethylene oxide) membranes containing silver nanoparticles," *Colloid and Polymer Science* 287(12):1425-1434, 2009.

Duan et al., "Electrospinning of chitosan solutions in acetic acid with poly(ethylene oxide)," *Journal of Biomaterials Science Polymer Edition* 15(6):797-811, 2004.

Geng et al., "Electrospinning of chitosan dissolved in concentrated acetic acid solution," *Biomaterials* 26(27):5427-5432, 2005.

Greiner et al., "Electrospinning: A Fascinating Method for the Preparation of Ultrathin Fibers," *Angewandte Chemie International Edition* 46(30):5670-5703, 2007.

Kampeerapappun, "The Design, Characteristics, and Application of Polyurethane Dressings Using the Electrospinning Process," doctoral dissertation, University of Akron, Ohio, 2008, 185 pages.

Abdelgawad et al., "Antimicrobial wound dressing nanofiber mats from multicomponent (chitosan/silver-NPs/polyvinyl alcohol) systems," *Carbohydrate Polymers* 100:166-178, 2014.

Agarwal et al., "Statistical optimization of the electrospinning process for chitosan/polylactide nanofabrication using response surface methodology," *J. Mater. Sci.* 47:4262-4269, 2012.

Areias et al., "Assessment of Parameters Influencing Fiber Characteristics of Chitosan Nanofiber Membrane in order to Optimize Fiber Mat Production," *Polymer Engineering and Science* 52(6):1293-1300, 2013.

Askari et al., "Fabrication of High Performance Chitosan/Polyvinyl Alcohol Nanofibrous Mat with Controlled Morphology and Optimized Diameter," *The Canadian Journal of Chemical Engineering* 9999:1-9, 2014.

Bhattarai et al., "Electrospun chitosan-based nanofibers and their cellular compatibility," *Biomaterials* 26:6176-6184, 2005.

Cai et al., "Fabrication of Chitosan/Silk Fibroin Composite Nanofibers for Wound-dressing Applications," *Int. J. Mol. Sci.* 11:3529-3539, 2010.

Cai et al., "Tailoring mechanical and antibacterial properties of chitosan/gelatin nanofiber membranes with $Fe_3O_4$ nanoparticles for potential wound dressing application," *Applied Surface Science* 369:492-500, 2016.

Çay et al., "Characterization and swelling performance of physically stabilized electrospun poly(vinyl alcohol)/chitosan nanofibers," *European Polymer Journal* 61:253-262, 2014.

Charernsriwilaiwat et al., "Electrospun chitosan-based nanofiber mats loaded with *Garcinia mangostana* extracts," *International Journal of Pharmaceutics* 452:333-343, 2013.

Charernsriwilaiwat et al., "Lysozyme-loaded, electrospun chitosan-based nanofiber mats for wound healing," *International Journal of Pharmaceutics* 427:379-384, 2012.

Chen et al., "Electrospinning of collagen-chitosan complex," *Materials Letters* 67:3490-3494, 2007.

Chen et al., "Electrospun collagen-chitosan nanofiber: A biomimetic extracellular matrix for endothelial cell and smooth muscle cell," *Acta Biomaterialia* 6:372-382, 2010.

Desai et al., "Morphological and Surface Properties of Electrospun Chitosan Nanofibers," *Biomacromolecules* 9:1000-1006, 2008.

Fuh et al., "Direct-write, highly aligned chitosan-poly (ethylene oxide) nanofiber patterns for cell morphology and spreading control," *Nanoscale Research Letters* 8(97): 1-9, 2013.

Ghani et al., "Fabrication of Electrospun Polyamide-6/Chitosan Nanofibrous Membrane toward Anionic Dyes Removal," *Journal of Nanotechnology* 2014(278418): 1-12, 2014.

Gholipour et al., "Optimization of chitosan-polyvinylalcohol electrospinning process by response surface methodology (RSM)," *e-Polymers* 035:1-9, 2010.

Homayoni et al., "Electrospinning of chitosan nanofibers: Processing optimization," *Carbohydrate Polymers* 77:656-661, 2009.

Huang et al., "Electrospinning of Amphipathic Chitosan Nanofibers for Surgical Implants Application," *Journal of Nanoscience and Nanotechnology* 12:5066-5070, 2012.

Ignatova et al., "Novel antibacterial fibers of quaternized chitosan and poly(vinyl pyrrolidone) prepared by electrospinning," *European Polymer Journal* 43:1112-1122, 2007.

(56) References Cited

OTHER PUBLICATIONS

Kang et al., "In Vivo Biocompatibility Study of Electrospun Chitosan Microfiber for Tissue Engineering," *Int. J. Mol. Sci. 11*:4140-4148, 2010.
Kiechel et al., "Non-covalent crosslinkers for electrospun chitosan fibers," *Carbohydrate Polymers 95*:123-133, 2013.
Klossner et al., "Correlation of Chitosan's Rheological Properties and Its Ability to Electrospin," *Biomacromolecules 9*:2947-2953, 2008.
Kriegel et al., "Electrospinning of chitosan-poly(ethylene oxide) blend nanofibers in the presence of micellar surfactant solutions," *Polymer 50*:189-200, 2009.
Lemma et al., "Preparation of Pure and Stable Chitosan Nanofibers by Electrospinning in the Presence of Poly(ethylene oxide)," *International Journal of Molecular Sciences 17*(1790)1-16, 2016.
Liu et al., "Fabrication and durable antibacterial properties of electrospun chitosan nanofibers with silver nanoparticles," *International Journal of Biological Macromolecules 79*:638-643, 2015.
Matsumoto et al., "Characterization of chitosan nanofiber fabric by electrospray deposition: Electrokinetic and adsorption behavior," *Journal of Colloid and Interface Science 310*:678-681, 2007.
Mendes et al., "Hybrid electrospun chitosan-phospholipids nanofibers for transdermal drug delivery," *International Journal of Pharmaceutics 510*:48-56, 2016.
Meng et al., "Fabrication, characterization and in vitro drug release behavior of electrospun PLGA/chitosan nanofibrous scaffold," *Materials Chemistry and Physics 125*:606-611, 2011.
Min et al., "Chitin and chitosan nanofibers: electrospinning of chitin and deacetylation of chitin nanofibers," *Polymer 45*:7137-7142, 2004.
Naseri et al., "Electrospun chitosan-based nanocomposite mats reinforced with chitin nanocrystals for wound dressing," *Carbohydrate Polymers 109*:7-15, 2014.
Naseri et al., "Porous electrospun nanocomposite mats based on chitosan-cellulose nanocrystals for wound dressing: effect of surface characteristics of nanocrystals," *Cellulose 22*:521-534, 2015.
Neamnark et al., "Electrospinning of hexanoyl chitosan," *Carbohydrate Polymers 66*:298-305, 2006.
Ogawa et al., "A New Polymorph of Chitosan," *Macromolecules 17*:973-975, 1984.
Ohkawa et al., "Electrospinning of Chitosan, Macromolecular Rapid Communications," 25(18):1600-1605, 2004.
Pakravan et al., "A fundamental study of chitosan/PEO electrospinning," *Polymer 52*:4813-4824, 2011.
Rathke et al., "Review of Chitin and Chitosan as Fiber and Film Formers," *J.M.S.-Rev. Macromol. Chem. Phys. C34*(3):375-437, 1994.
Sangsanoh et al., "In vitro biocompatibility of electrospun and solvent-cast chitosan substrata towards Schwann, osteoblast, keratinocyte and fibroblast cells," *European Polymer Journal 46*:428-440, 2010.
Santos et al., "Preparation and characterization of polysaccharides/PVA blend nanofibrous membranes by electrospinning method," *Carbohydrate Polymers 99*:584-592, 2014.
Sarhan et al., "High concentration honey chitosan electrospun nanofibers: Biocompatibility and antibacterial effects," *Carbohydrate Polymers 122*:135-143, 2015.
Schiffman et al., "One-Step Electrospinning of Cross-Linked Chitosan Fibers," *Biomacromolecules 8*:2665-2667, 2007.
Sedghi et al., "Biocompatible electrospinning chitosan nanofibers: A novel delivery system with superior local cancer therapy," *Carbohydrate Polymers 159*:1-10, 2017.
Sencadas et al., "Determination of the parameters affecting electrospun chitosan fiber size distribution and morphology," *Carbohydrate Polymers 87*:1295-1301, 2012.
Tang, "Carboxymethyl chitosan-zinc(II) phthalocyanine conjugates: synthesis, characterization and photodynamic antifungal therapy," Manuscript Draft, Carbohydrate Polymers, 2004. (40 pages).
Teng et al., "Blend fibers of chitosan-agarose by electrospinning," *Materials Letters 63*:2510-2512, 2009.
Van der Schueren et al., "Polycaprolactone/chitosan blend nanofibers electrospun from an acetic acid/formic acid solvent system," *Carbohydrate Polymers 88*:1221-1226, 2012.
Varnaitè-Žuravliova et al., "Electrospinning of Chitosan Biopolymer and Polyethylene Oxide Blends," *AUTEX Research Journal*, pp. 1-15, 2019.
Xu et al., "Preparation of chitosan/PLA blend micro/nanofibers by electrospinning," *Materials Letters 63*:658-660, 2009.
Zhang et al., "Chitosan Nanofiber from an Easily Electrospinnable UHMWPEO-Doped Chitosan Solution System," *Biomacromolecules 9*:136-141, 2008.
Zhang et al., "Electrospun biomimetic nanocomposite nanofibers of hydroxyapatite/chitosan for bone tissue engineering," *Biomaterials 29*:4314-4322, 2008.
Zhang et al., "Centrifugal Spinning: An Alternative Approach to Fabricate Nanofibers at High Speed and Low Cost," *Polymer Reviews 54*:677-701 (2014).
Du et al., "Cellulose/chitosan hybrid nanofibers from electrospinning of their ester derivatives," *Cellulose 16*: 247-260, 2008.
Wang et al., "Nanofiber Fabrication Techniques and its Applicability to Chitosan," *Progress in Chemistry 26*(11): 1821-1831, 2014.
Chen et al., "Diameter Control of Electrospun Chitosan-Collagen Fibers," *Journal of Polymer Science: Part B: Polymer Physics 47*:1949-1955, 2009.

\* cited by examiner

| Formula ID | Chitosan code | %chitosan | %acetic acid | %water | %RM | RM type | %RM/(%RM + %CH) | Viscosity (Pa.s) |
|---|---|---|---|---|---|---|---|---|
| 1 | Chitosan-1 | 6.1 | 67.5 | 26.4 | 0 | NA | 0 | 2.6 |
| 2 | Chitosan-1 | 6.1 | 60 | 33.9 | 0 | NA | 0 | 1.7 |
| 3 | Chitosan-2 | 7.5 | 9.25 | 83.25 | 0 | NA | 0 | 2.49 |
| 4 | Chitosan-6 | 3.1 | 9.7 | 87.2 | 0 | NA | 0 | 49 |
| 5 | Chitosan-2 | 5.4 | 9.4 | 77.5 | 7.7 | PVA | 0.59 | 7.2 |
| 6 | Chitosan-2 | 5.4 | 9.4 | 81.3 | 3.9 | PVA | 0.41 | 1.7 |
| 7 | Chitosan-1 | 3.8 | 87 | 9.2 | 0 | NA | 0 | 0.34 |
| 8 | Chitosan-1 | 4.3 | 86.6 | 9.1 | 0 | NA | 0 | 0.89 |
| 9 | Chitosan-1 | 4.8 | 86.1 | 9.1 | 0 | NA | 0 | 3.39 |
| 10 | Chitosan-1 | 4.9 | 54.2 | 40.3 | 0.6 | PEO-1 | 0.11 | 0.94 |
| 11 | Chitosan-1 | 5.8 | 53.7 | 39.8 | 0.7 | PEO-1 | 0.11 | 2.4 |
| 12 | Chitosan-2 | 4.9 | 54.2 | 40.3 | 0.6 | PEO-1 | 0.11 | 10.33 |
| 13 | Chitosan-2 | 5.8 | 53.7 | 39.8 | 0.7 | PEO-1 | 0.11 | 4.06 |
| 14 | Chitosan-1 | 4.5 | 60.6 | 34.5 | 0.4 | PEO-1 | 0.08 | 0.75 |
| 15 | Chitosan-2 | 4.9 | 54.2 | 40.3 | 0.6 | PEO-1 | 0.11 | 2.3 |
| 16 | Chitosan-2 | 5.8 | 53.7 | 39.8 | 0.7 | PEO-1 | 0.11 | 6.5 |
| 17 | Chitosan-2 | 6.7 | 53.1 | 39.4 | 0.8 | PEO-1 | 0.11 | 71 |
| 18 | Chitosan-2 | 6.2 | 54.1 | 39.4 | 0.3 | PEO-2 | 0.05 | 11.5 |
| 19 | Chitosan-6 | 2 | 54.3 | 43.7 | 0 | NA | 0 | 2.4 |
| 20 | Chitosan-2 | 6.7 | 53.1 | 39.4 | 0.8 | PEO-1 | 0.11 | 66 |
| 21 | Chitosan-2 | 7.6 | 49.8 | 41.7 | 0.9 | PEO-1 | 0.11 | 69.7 |
| 22 | Chitosan-3 | 4.9 | 54.2 | 40.3 | 0.6 | PEO-1 | 0.11 | 599 |
| 23 | Chitosan-2 | 4 | 54.2 | 41.3 | 0.5 | PEO-1 | 0.11 | 230 |
| 24 | Chitosan-6 | 3.1 | 54.2 | 42.3 | 0.4 | PEO-1 | 0.11 | 91 |
| 25 | Chitosan-2 | 6.7 | 13 | 79.5 | 0.8 | PEO-1 | 0.11 | 120 |
| 26 | Chitosan-2 | 6.7 | 53.1 | 39.4 | 0.8 | PEO-1 | 0.11 | 70 |

FIG. 1A

| Formula ID | Chitosan code | %chitosan | %acetic acid | %water | %RM | RM type | %RM/(%RM + %CH) | Viscosity (Pa.s) |
|---|---|---|---|---|---|---|---|---|
| 27 | Chitosan-2 | 4.9 | 54.2 | 40.3 | 0.6 | PEO-1 | 0.11 | 1.86 |
| 28 | Chitosan-2 | 6.7 | 53.1 | 39.4 | 0.8 | PEO-1 | 0.11 | 32 |
| 29 | Chitosan-2 | 6.7 | 53.1 | 39.4 | 0.8 | PEO-1 | 0.11 | 44 |
| 30 | Chitosan-2 | 7.1 | 55.9 | 36.1 | 0.9 | PVP | 0.11 | 46 |

FIG. 1B

| Formula ID | Machine | Spin (Y or N) | RPM Spin | Temp. (°C) | Humidity (%) | Fiber Diam. (nm) | Pore Diam. (μm) | Notes |
|---|---|---|---|---|---|---|---|---|
| 1 | L-1000 | N | NA | 21-22 | 44-61 | NA | NA | |
| 2 | L-1000 | N | NA | 21 | 45.1 | NA | NA | |
| 3 | L-1000 | N | NA | 23 | 44.5 | NA | NA | |
| 4 | L-1000 | N | NA | 23 | 44.6 | NA | NA | |
| 5 | L-1000 | N | NA | 23 | 44.4 | NA | NA | |
| 6 | L-1000 | N | NA | 23 | 44.5 | NA | NA | |
| 7 | L-1000 | N | NA | 27 | 50.1 | NA | NA | |
| 8 | L-1000 | N | NA | 28 | 50 | NA | NA | |
| 9 | L-1000 | N | NA | 28 | 50 | NA | NA | |
| 10 | L-1000 | Y | 4000 | 25 | 52 | - | 1-8 | Good spinning |
| 11 | L-1000 | Y | 4000 | 25 | 47 | - | 2-8 | High production efficiency |
| 12 | L-1000 | Y | 4000 | 25 | 48 | - | 1-8 | High production efficiency |
| 13 | L-1000 | Y | 4000 | 24 | 51 | - | 2-8 | Good production efficiency |
| 14 | L-1000 | N | NA | - | - | NA | NA | |
| 15 | L-1000 | Y | 4000 | 32 | 44-49 | <2000 | 1-8 | Fiber breakage above 4000 rpm |
| 16 | L-1000 | Y | 5000 | 44-53 | 29-42 | <2000 | 1-4 | Fiber breakage above 5000 rpm |
| 17 | L-1000 | Y | 7000 | 24 | 49 | <2000 | 2-8 | Excellent spinning at all rpm (4000 - 7000) |
| 18 | L-1000 | Y | 5000 | 32-34 | 33-35 | <2000 | 1-10 | Good spinning from 4000 - 6000 rpm |
| 19 | L-1000 | N | | 34-37 | 38-43 | <2000 | - | Solution produced gels & did not spin |
| 20 | L-1000 | Y | 5000 | 32-40 | 30-43 | 300-600 | 2-10 | 0.335 g of citric in H2O; spinning proceeded well |
| 21 | L-1000 | Y | 5000 | 43-44 | 24-27 | 1000-10000 | 2-20 | 11.8 g of 85-90% lactic in H2O |
| 22 | L-1000 | Y | 5000 | 34-45 | 24-38 | 300 | 2-8 | Low spinning efficiency |
| 23 | L-1000 | Y | 5000 | 35 | 35 | 300-800 | 2-8 | Spinning proceeded well with fibers 300 - 800 nm |

FIG. 2A

| Formula ID | Machine | Spin (Y or N) | RPM Spin | Temp. (°C) | Humidity (%) | Fiber Diam. (nm) | Pore Diam. (μm) | Notes |
|---|---|---|---|---|---|---|---|---|
| 24 | L-1000 | Y | 5000 | 38 | 32 | 300-500 | 1-15 | Spinning proceeded well with fibers 300 - 500 nm |
| 25 | FE1.1** | Y | 7000-9000 | 25-28 | 38-48 | 100-400 | 1-7 | 17.6 g/m2 multilayer |
| 26 | FE1.1*** | Y | 7000-8000 | 34-37 | 33-40 | 200-700 | 1-8 | 3.6 g/m2 |
| 27 | FE1.1* | Y | 7000-9000 | 34-37 | 33-40 | 100-2000 | 1-4 | 2.0 g/m2; good efficiency |
| 28 | FE1.1* | Y | 7000 | 34-37 | 33-40 | 100-1000 | 2-8 | 3.4 g/m2; good efficiency |
| 29 | FE1.1* | Y | 8000-10000 | 34-37 | 47 | 200-3000 | 1-3 | 2.2 - 4.0 g/m2; good efficiency |
| 30 | FE1.1* | N | NA | 34-37 | NA | 100-1000 | NA | |

*25 cm/min feed
**10 cm/min feed
***20 cm/min

*FIG. 2B*

CHITOSAN SUPERFINE FIBER SYSTEMS

RELATED APPLICATIONS

This application claims priority to U.S. provisional patent application Ser. No. 62/294,994, filed on Feb. 12, 2016, the contents of which are fully incorporated herein by reference.

STATEMENT REGARDING FEDERALLY SPONSORED RESEARCH OR DEVELOPMENT

This invention was made with government support under Grant No. 1R43DK104564-01 (revised) awarded by the National Institutes of Health. The government has certain rights in the invention.

FIELD OF THE INVENTION

The present chitosan-based superfine fiber invention relates to compositions, formulations, and processes that result in numerous significant advantages for the production and use of superfine fiber bioactive matrices in biomedical applications. The present chitosan-based superfine fiber of the invention is spun from a solution composition comprising non-volatile chitosan polymer(s); volatile, semi-volatile or non-volatile acid component(s); optional non-volatile diluent polymer component(s) that assist(s) with the fiber spinning process; optional cross-linking component(s) that crosslink(s) the spun polymer fiber after spinning and drying; and water. Additives may be included in low percentage (less than or equal to 5% by mass of the dry fiber) in the fiber spinning solution to provide for wetting changes to the chitosan, plasticization of the fiber, degradation of the fiber, and active substance release from the fiber. Also, the chitosan material of the solution may be modified to provide for enhancements in wetting, adhesion and bioactivity at pH other than less than pH 6.5. The present invention relates to superfine, chitosan-based fibers, wherein the chitosan-based fiber spun from a suitable spinning solution have a percentage chitosan content of at least about 20% w/w, and highly conformable and compliant matrices comprising such fibers, processes for their production, and related formulations. The superfine chitosan-based fibers of the invention preferably include microfibers with diameter less than or equal to about 10 microns and micron and submicron fibers that are about 2 microns and less.

INVENTION SUMMARY

The present chitosan-based superfine fiber invention includes compositions, formulations, and processes that result in numerous significant advantages for the production and use of superfine fiber bioactive matrices in biomedical applications. The present invention relates to superfine, chitosan-based fibers, wherein the chitosan-based fibers have a percentage chitosan content of at least about 20% w/w, and highly conformable and compliant matrices comprising such fibers, processes for their production, and related formulations. The superfine chitosan-based fibers of the invention preferably include microfibers with diameter less than or equal to about 10 microns, about 9 microns, about 8 microns, about 7 microns, about 6 microns, about 5 microns, about 4 microns, about 3 microns, and submicron fibers that are about 2 microns or 1 micron and less. The superfine chitosan-based fibers with chitosan content of at least about 20% w/w of the present invention may comprise all of the composition (i.e. about 90 to 100% (w/w)), substantially all of the composition (i.e. about 70 to 90% (w/w)), about one half of a composition (i.e. about 50% (w/w)), or less than one half of a composition (i.e. less than 50% (w/w)). Compositions of the present invention may comprise various amounts of superfine chitosan-based fiber content; however, in most cases the superfine chitosan-based fiber content of a composition preferably will be at least 50% (w/w).

Benefits and advantages realized by the present invention generally relate to, in one aspect, commercially processable, new chitosan-based superfine fibers, and various new matrices, including nonwoven and woven forms, comprising these fibers that present a significantly improved bioactive surface with high specific surface area in a biological cell porous superfine fiber matrix with at least 80% void volume that is, optionally, also highly conformable when wet to injured tissue surfaces and shows low to no shrinkage or swelling in a contact with said injured tissue. Bioactive surfaces are surfaces composed of bioactive materials that present chemical functionality that is able to locally activate, moderate, or passivate biological systems and processes. Chitosan presents substantial bioactive functionality due to the presence of positively charged carbon-2 ammonium functionality in its glucosammonium monomer at aqueous solution pH less than 6.5 and when an acid salt is present. Additional advantages of the present invention relate to the preservation of the chitosan acid salt including for example increased bioactivity and optional adherence of the material to wet or moist surfaces without the use of a separate adhesive. Additional advantages to the present inventive superfine fibers include resultant faster drying of the superfine fibers compared to conventional spinning which, in turn, stabilizes the fibers, improves the integrity of the fibers, and facilitates their immediate collection, layering, weaving, matting, etc., into nonwoven or woven product forms.

Benefits and advantages realized by the present invention also generally relate to, in additional aspects, the new chitosan solution formulations and new production methods for making the chitosan-based superfine fibers and fiber products using centrifugal spinning.

Centrifugal spinning of chitosan solution formulations to form the superfine fibers of the present invention and the compositions formed by this process result in significant process and product advantages over, for example, fiber production techniques dependent on use of a high voltage field (electrospinning) to initiate and propagate fiber formation. That is, the chitosan solution formulations of the present invention provide for the preparation of chitosan fiber that can be collected and formed into new nonwoven or woven superfine fiber matrices. These matrices are useful for their bioactive functionality in fields including, among other things, tissue engineering, regenerative medicine and wound care applications to promote bleeding control, heal wounds, regrow tissue, provide antibacterial properties, and deliver therapeutic active agents.

The processeable fiber diameter range from the centrifugal spinning includes micron to submicron diameter of the bioactive chitosan-based superfine fiber that is advantageous for realizing high spinning rates of bioactive fiber as well as for allowing promotion of highly desirable pore sizes in the collected nonwoven fiber matrices. Spinning rate through one or more spinnerets on a spinning head is proportional to cross-sectional area of the spun fiber. Pore size in nonwoven spun fiber matrices is proportional to mean fiber diameter and range of fiber diameter. It is expected that the presence of pores in the nonwoven spun fiber matrix would require buildup of at least 10 to 50 layers of fiber. The presence of these at least 10 to 50 layers of fiber in an exemplary matrix may be assumed in connection with this description of nonwoven matrix characteristics such as internal structure and pore size. To realize pore structure the superfine chitosan-based fibers of the nonwoven matrix should have at least 0.1 g/m² basis weight. Notably, pore size ranges as discussed herein which relate to SEM micrographs that are measured by looking at the pores and with the size range determined by the longest (L) and shortest (S) length of access through the center of the pore so as long as L/S is greater than or equal to 2; otherwise, size range was determined by measuring the diameter of a circle that would fit within an open space bordered by adjacent fibers. These measurements for determination of pore sizes provide a reliable estimation of pore size range for both dry and wet chitosan-based superfine fiber matrices because these materials do not collapse upon wetting and do not demonstrate significant (i.e. greater or less than about 10%, or 5%) dimensional changes upon wetting with a fluid such as biological fluids including blood or plasma. Also, this method of SEM pore size measurement with a fluid determination is significantly more reliable than intrusive measurement of pore size such as by mercury intrusion porosity because this method of measurement applies significant pressure on and may destroy the delicate pore structure of superfine-based fibers, microfibers, and nanofibers such as those described herein.

Too small a diameter of individual, randomly overlaid, non-aligned fibers with mean fiber diameter less than or equal to 500 nm in the nonwoven fiber matrix results in matrix mean pore diameters less than or equal to 1.5 microns which are not conducive to pores which allow for infiltration of cells. Typical diameter of red blood cells, platelets, neutrophils, lymphocytes, fibroblasts and chondrocytes are about 8, 3, 10, 15, 12 and 20 microns respectively. Accordingly, preferred optimal pore sizes of matrices according to the present invention may be about 5 to 40 microns to accommodate the infiltration of different cell sizes within a matrix. Centrifugal spinning allows for a selection of mean fiber size such as about 0.4 to 7 microns which will provide mean pore size near 1 to 25 microns in a nonwoven fiber matrix for efficient accommodation of infiltration by different cells and optimal matrix surface contact with the cells.

Additionally, the bioactive superfine chitosan-based fibers in their nonwoven and woven format present a permeable, highly specific, positively charged surface. This positively charged surface creates a highly reactive surface for strong and close interaction with biopolymers, tissues and cells possessing inherent negative charge. Such negatively charged biopolymers, tissues and cells include other polysaccharides, proteins, tissue mucosa, injured tissue surfaces, red blood cells, platelets, bacteria and viruses. As an example of this bioactive interaction, red blood cell and platelet membranes with strong anionic negative charge are attracted to the superfine chitosan-based fibers where they can bind closely to the chitosan. This close binding can stimulate further interaction such as platelet activation. The cellular membranes fuse to superfine chitosan-based fibers upon contact. Accordingly, a clot can be formed very quickly, circumventing the immediate need for clotting proteins that may otherwise be required for hemostasis. For this reason, the superfine chitosan-based fibers of the present invention can be effective for both normal as well as anti-coagulated individuals, and as well as persons having a coagulation disorder like hemophilia. Notably, the superfine chitosan-based fibers of the present invention may also bind bacteria, endotoxins, and microbes, and can kill bacteria, microbes, and/or viral agents on contact.

Because the bioactive superfine chitosan-based fibers of the present invention attract red blood cell membranes, which fuse to the fibers upon contact, a clot can be formed very quickly. The presence of the chitosan superfine chitosan-based fibers in a nonwoven or woven form during a bleeding episode of a person having hemophilia or another coagulation disorder can accelerate the clotting process independent of the clotting cascade, which, in such people, is in some way compromised. For this reason, the superfine chitosan-based fibers of the present invention can be effective as an interventional tool for persons having a coagulation disorder like hemophilia.

Centrifugal spinning, as used in the present invention, allows higher spinning rates and throughput or mass flow (>1 g/min) through individual spinnerets as more formulation material can be processed in a shorter amount of time when compared to conventional electrospinning techniques. The centrifugal spinning of superfine fiber techniques and formulations of the present invention also beneficially allow for the ready, one-step, or one spinning cycle (which may be continuous) higher product basis weights (greater than about 1 g/m² relative to conventional electrospun chitosan-based superfine fiber products). Further, the present invention formulations and centrifugal spinning techniques can be used to prepare fibers without the deleterious process steps associated with conventional spinning solution techniques that include spinning directly into coagulation, neutralization or precipitation baths and other handling steps such as fiber drawing (which compromise the chemical integrity and bioactivity of the spun chitosan fibers).

Also, fibers prepared from solution using conventional spinning methods of die extrusion into coagulation, neutralization or precipitation baths cannot be formed into superfine fibers and their fiber diameter generally is not less than 10 microns.

It is noted that, in contrast to the present invention, prior art electrospun superfine chitosan fibers spun from a single spinneret with a percentage of chitosan greater than about 20% w/w suffer from unacceptably low spinning rates (generally at or below about 0.01 g/min per spinneret), concomitant low spun matrix basis weights (i.e., generally at or below about 0.1 g/m²) and commercially unacceptable variability in rate of collection nonwoven fiber at a sufficient basis weight collection above about 5 g/m² due to the blocking or interfering effect of the collected material on the high voltage electric field.

BACKGROUND OF THE INVENTION

For over 3000 years, the finest fiber has been natural silk fiber produced by the mulberry silkworm (an insect) with a denier (thickness or mass in gram per 9000 meters) close to 1.0. Fine fibers are highly desirable due to their ability to be formed into supple and conformable nonwoven and woven items with high specific surface area. In more recent times, mass-produced, fine, synthetic polyester fibers have been produced with denier close to silk. Because organic fibers, such as silk and polyester have similar flexural modulus (resistance to flexure per cross-sectional area) characteristics, fiber diameter is often applied as a reliable indicator of drape suppleness and conformability. The finest silk fibers are between 5-10 microns in diameter while the finest conventionally spun polyester fibers are not less than 10 microns in diameter and most often more than 10 microns in diameter. Fine fibers with diameter near and less than fine silk fiber diameter produced from the silkworm, i.e., fiber less than or equal to 10 microns in thickness, may be referred to as superfine fiber.

The superfine chitosan-based fibers of the present invention are preferably fibers with diameter less than or equal to 10 microns.

Because of technological limitations with conventional spinning techniques, modern nonwoven and woven wound dressing articles have fiber diameters of no less than about ten microns in diameter. Also, conventional spinning from aqueous solution systems typically requires spinning directly into coagulation or precipitation baths and other handling steps such as fiber drawing which compromise the chemical integrity of the spun fibers. For example, in conventional chitosan-based fiber spinning, the fiber formulation is an aqueous acid solution that is spun directly into a caustic solution (typically concentrated NaOH) precipitation bath which results in the immediate loss of precipitated chitosan fiber acid functionality. Specifically, in the case of chitosan polymers, including spun chitosan-based fibers, chitosan neutralization above a 6.3 pH results in a loss of all glucose ammonium positively charged (polycationic) activity, i.e., a loss in bioactivity. Similar to conventional spinning of polyester fiber, conventional spinning of chitosan fiber produces fibers with finest diameter of not less than 10 microns.

In one embodiment, the superfine chitosan-based fibers of the present invention have a diameter less than or equal to 10 microns and/or micron and submicron fibers that are about 2 microns and less.

To date, the only non-insect based method available for preparation of bioactive matrices composed of superfine fibers has been electrospinning with centrifugal spinning now providing an additional approach. As further detailed below, production of superfine fiber matrices for wound care by electrospinning has proven infeasible or impracticable outside of small-scale research and development use. Although there are many examples of electrospun superfine fiber matrices formed from bioactive polymers such as chitosan described in the patent literature (see U.S. patent application Ser. No. 12/590,712, Chinese Patent CN1238061 and U.S. Pat. Nos. 6,753,454, 7,134,857, 7,592,277, 9,194,058, and 9,163,338), none of these examples has been translated to a commercial wound care product. Crude electrospinning of superfine fibers from solvent solution by application of a high voltage field across a spinning fluid were first described by J. F. Cooley in U.S. Pat. No. 692,631 and W. J. Morton in U.S. Pat. No. 705,691 in 1902. Anton Formhals patented improved electrospinning processes (U.S. Pat. Nos. 1,975,504, 2,077,373, 2,109,333, 2,116,942, 2,123,992, 2,158,415, 2,158,416, 2,160,962, 2,187,306, 2,323,025, and 2,349,950) between 1934 and 1944. More recent innovations in electrospinning include U.S. Pat. Nos. 7,585,437, 6,713,011, and 6,106,913.

Electrospinning relies on the dielectric susceptibility of the fluid being spun, either as a solution or a melt, to a charged local field when a constant high voltage field, typically significantly greater than a kilovolt (kV), is applied across the fluid surface that is connected to one electrode. The electric field acceleration applied to the charged fluid surface is able to overcome fluid surface tension with the reduction in the fluid surface energy providing release of particle (bead) or fiber stream from the fluid surface. The charged stream is propelled away from the electrode contacting the fluid surface towards the separate oppositely charged electrode. The competition between particle and fiber formation is determined by a balance between the cohesive viscoelasticity of the fluid and the electrospun fiber which, if sufficiently great, is able to overcome the surface tension promotion of particle formation. A solid surface collector may be applied between the oppositely charged local surface and the charged stream to capture the streaming material. Continuous spinning of a single filament in electrospinning may be performed by flow of fluid (solution or melt) through an orifice or needle with the orifice (needle) acting as the fiber initiating electrode.

In addition to the unacceptably low rate of fiber deposition from needle electrodes (also sometimes referred to as nozzle electrodes), electrospinning from needle and needle-less electrodes experiences serious problems of high voltage field instability and material flow non-homogeneity or lack of uniformity that occur during the electrospinning process as material is deposited between the electrodes. This voltage field instability related to mass flow creates uncertainty and variability in the production output which is unacceptable for fiber-based products. This is especially relevant to the production of medical products since the inability to control process leads to unacceptable product variability. In electrospinning, the electrical field strength and uniformity declines with deposition and collection of fiber matrix which acts as electrical insulation between the two spinning electrodes. Build-up of a collected nonwoven fiber basis weight greater than about 0.5 $g/m^2$ begins to impede mass flow requiring increase in voltage to maintain a uniform collection rate. At basis weights of collected nonwoven fiber greater than about 5 $g/m^2$ total loss of fiber spinning can occur. At basis weights greater than 20 $g/m^2$, the voltages required to initiate (primarily in the case of needle-less electrode spinning) and maintain spinning (both needle and needle-less spinning) can be so large (>100,000 volts) that any nearby earthed conductive surface will become charged providing for dangerous and destructive high voltage discharge effects, such as, burning of collected superfine fibers, etc.

A more recent development in electrospinning is the use of a rotating mandrel electrode (needle-less electrode) as the fiber initiating electrode is able to be wet by the spinning fluid with the ability to produce spontaneous fiber streaming without needles (U.S. Pat. No. 7,585,437). In electrospinning from individual needle spinnerets, the rate of superfine fiber mass flow from each spinneret is less than about 0.01 g/min, and often less than to 0.001 g/min, with concomitantly low basis weight material output (generally less than about 0.1 $g/m^2$ in one hour of spinning onto a surface of about 1 square meter). The spinning mandrel electrode provides for up to about 10,000 fibers able to be spun at the same time from one electrospinning mandrel and thus may provide some remediation to the severely low yields experienced by the electrospinning approach to produce superfine fiber. It is noted, however, that U.S. Pat. No. 7,585,437 is silent as to chitosan-based fiber preparation and production stability in spinning and collecting nonwoven fiber basis weights above about 0.5 $g/m^2$, above about 5 $g/m^2$ and above about 20 $g/m^2$.

These problems of disrupted mass flow and electrical field instability significantly limit the applicability of electrospinning for commercial applications including, for example, the production of wound care dressings, drug delivery platforms and tissue engineering matrices with fiber basis weight requirements preferably greater than about 1 $g/m^2$, more preferably greater than about 5 $g/m^2$, greater than about 8 $g/m^2$, greater than about 10 $g/m^2$, greater than about 12 $g/m^2$, greater than about 14 $g/m^2$, greater than about 16 $g/m^2$, greater than about 18 $g/m^2$, and still more preferably greater than about 20 g/m², greater than about 25 g/m², greater than about 30 g/m², greater than about 35 g/m², greater than about 40 g/m², greater than about 45 g/m² and most preferably greater than about 50 g/m².

An alternate approach to commercial spinning of superfine fiber to produce materials with a fiber basis weight greater than about 5 g/m² has emerged with recent refinements in centrifugal spinning techniques including Force Spinning (U.S. patent application Ser. No. 13/953,097, U.S. Pat. Nos. 8,231,378, 8,647,540, 8,647,541, 8,658,067, 8,709,309, 8,777,599, 8,721,319, 8,778,240, 8,828,294, and 8,858,845) and non-Force Spinning (U.S. Pat. Nos. 8,303,874, 5,494,616, 5,460,498, 4,790,736 and 4,311,570). But successful centrifugal spinning of chitosan-based superfine fibers chitosan content greater than about 20% w/w has not yet been previously reported. Nonetheless, these centrifugal techniques may be able to produce superfine fiber with individual spinneret stream spinning rates of grams/minute without requiring applied voltage across the spinning fluid. Independent from high voltage electric field variability, a centrifugal spinning system is able to spin its homogeneous fluid into superfine fiber continuously at the rate of flow of the homogeneous fluid trough the spinneret(s) and without the flow affected by how much fiber has been collected previously. The initiation of fiber streaming in centrifugal spinning is controlled through a spinneret (or outer rotor surface fluid release element) with initiation in spinning being dependent on, for example, spinneret rotational velocity, spinning fluid surface tension, radius of spinneret orifice, and spinning fluid viscoelasticity. Following fiber stream extension streaming initiation, the final superfine fiber diameter is dependent on the spinneret orifice radius, collector fluid against fiber stream shear rate, fiber stream solidification rate in the collector fluid (drying rate in the case of spinning a solution and cooling rate in the case of spinning a melt), fiber stream viscoelasticity in the collector fluid and the distance traveled radially and tangentially before hard surface collection. The term solidification is used here to describe a process to cause a material to become a solid so that it is non-fluid in that application of a moderate force (for instance 1 g) per size of the material (per one kilogram) to the material will not displace the material or cause a significant deformation to the material. Typically, an inert and dry collecting fluid at controlled temperature such as dry air is used in collection and in fiber solidification (drying of a solution or cooling of a melt), however other inert gases or liquids may be used. Alternate inert fluids may include carbon dioxide, nitrogen, argon, and their combinations. In centrifugal spinning of a solution containing a non-volatile component and a volatile component, the drying fluid may contain a fraction of the volatile component to slow the rate of drying to provide for enhanced solute fiber extension. The hard surface collection system may be a stationary or mobile collector system positioned at a set radial distance from the rotating spinneret. A stationary system is most often a series of equally spaced columns oriented perpendicular to the path of travel of the fiber from the spinneret to efficiently collect the fiber. A mobile system is most often a conveyer belt with the belt perpendicular across the path of travel of the fiber from the spinneret, thus allowing for efficient capture.

As in the case of electrospinning different compositions of spinning fluid formulations, successfully spinning a fluid formulation into a superfine fiber by centrifugal spinning is often severely limited due to difficulties in both fiber initiation and fiber extension. Since fiber initiation and fiber extension concern essentially different processes in centrifugal spinning compared to electrospinning, the solution, or fluid formulation, conditions and compositions used to successfully electrospin superfine fiber generally cannot be relied upon to successfully centrifugally spin the same superfine fiber. One physical requirement common to spinning, independent of spinning methodology, is that a polymeric fluid being spun, if it is to be successfully spun, must have sufficient intermolecular overlap or entanglement between polymer molecules (high enough viscosity) with sufficiently low surface tension during the fiber initiation process that provides for promotion of fiber rather than individual droplet formation.

Successful centrifugal spinning of chitosan-based superfine fibers with chitosan content greater than about 15% w/w has not been previously reported. The only literature reports of attempted spinning of chitosan (Xu et al. 2014a; Xu et al. 2014b) titled "Large-scale Production of a Ternary Composite Nanofiber Membrane for Wound Dressing Applications" and "Development of Tannic acid/Chitosan/Pullulan Composite Nanofibers from Aqueous Solution for Potential Applications as Wound Dressing," respectively, are with chitosan-based superfine fiber having a chitosan content of less than 20% w/w. Both these reports are from the same University of Texas group that developed the Force Spinning centrifugal process. Other than including very low fractions w/w of chitosan in the final superfine fibers of the nonwoven structures (7.9% and 12.5% respectively), Xu et al 2014a and Xu et al. 2014b provided a substantial stoichiometric excess of non-volatile polyanionic citric acid 26.3% and 12.5% w/w respectively in the reported studies. This polyanionic excess converted all the desirable cationic activity associated with the presence of chitosan to anionic matrix activity in the final dried nonwoven fiber matrices. Addition of tannic acid to the mixture in two additional arms only compounds this focus on anionic activity and further loss of any possible benefit of the presence of chitosan in the composition. Other noted differences of the Xu et al. materials compared to those of the invention are that water soluble polymers polyvinylalcohol and pullulan make up substantially the bulk of both compositions 65.8% and 75% w/w respectively. Both these highly water soluble polymers require significant crosslinking to resist water dissolution of the matrix dressing. Typically a high level of crosslinking is undesirable in a bioactive material as crosslinking reduces the functional capability of the polymer to interact with cells.

BRIEF DESCRIPTION OF THE DRAWINGS

The invention may be more clearly understood from the following description of embodiments thereof, given by way of example only, with reference to the accompanying drawings. Note that throughout this document, reference to figures including identification by either an upper or lower case letter is meant to indicate the same figure regardless of whether an upper or lower case letter is used.

FIGS. 1a and 1b. Table of test spinning formulation solutions and their viscosities. The formulas identified throughout the specification refer to the formulas described in the table of FIGS. 1a and 1b.

Figures to 2a and 2b. Table of spinning formulation solutions outcomes of spinning of the formulations and spinning conditions.

Figure 3A:
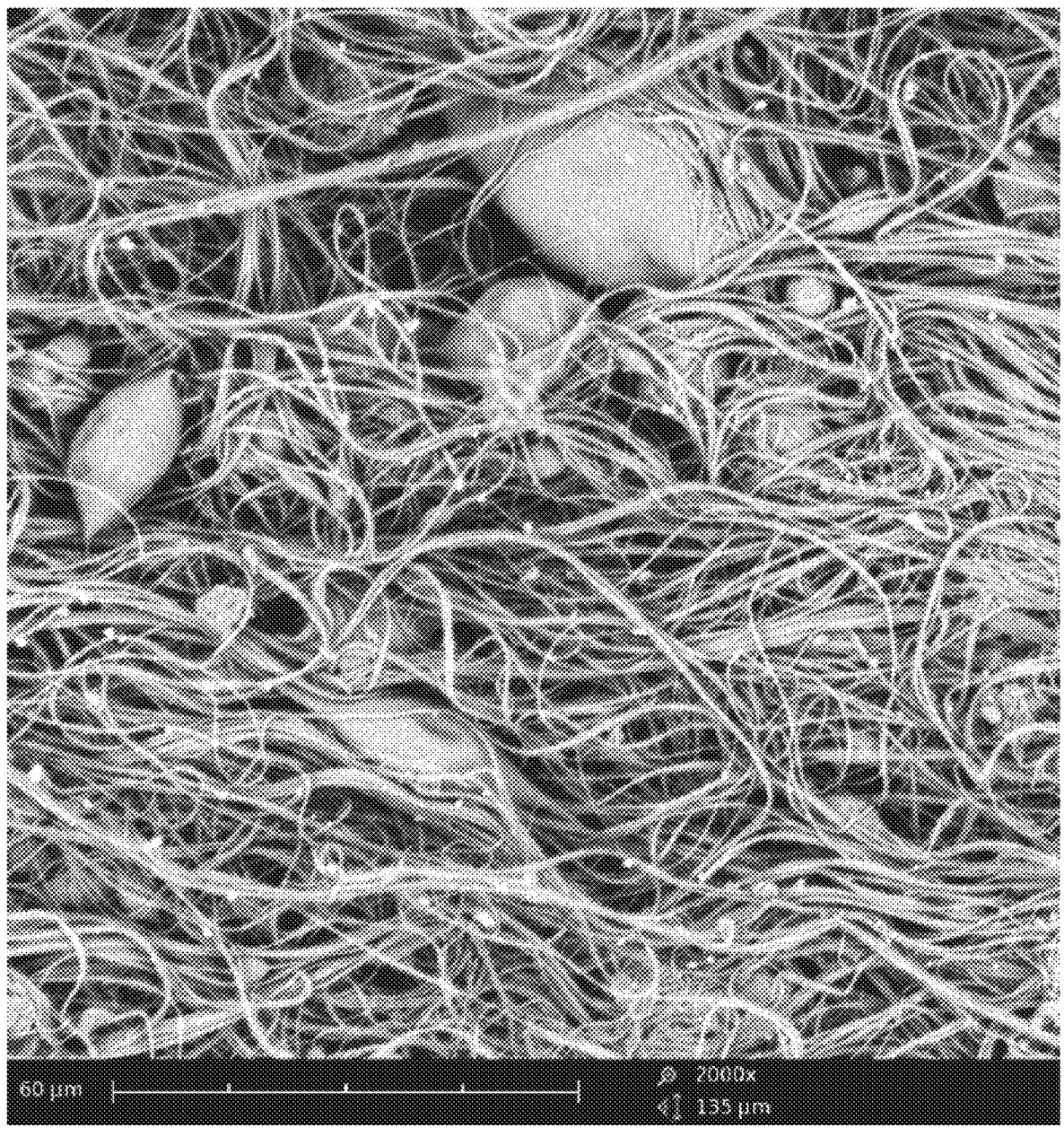
Figure 3B:
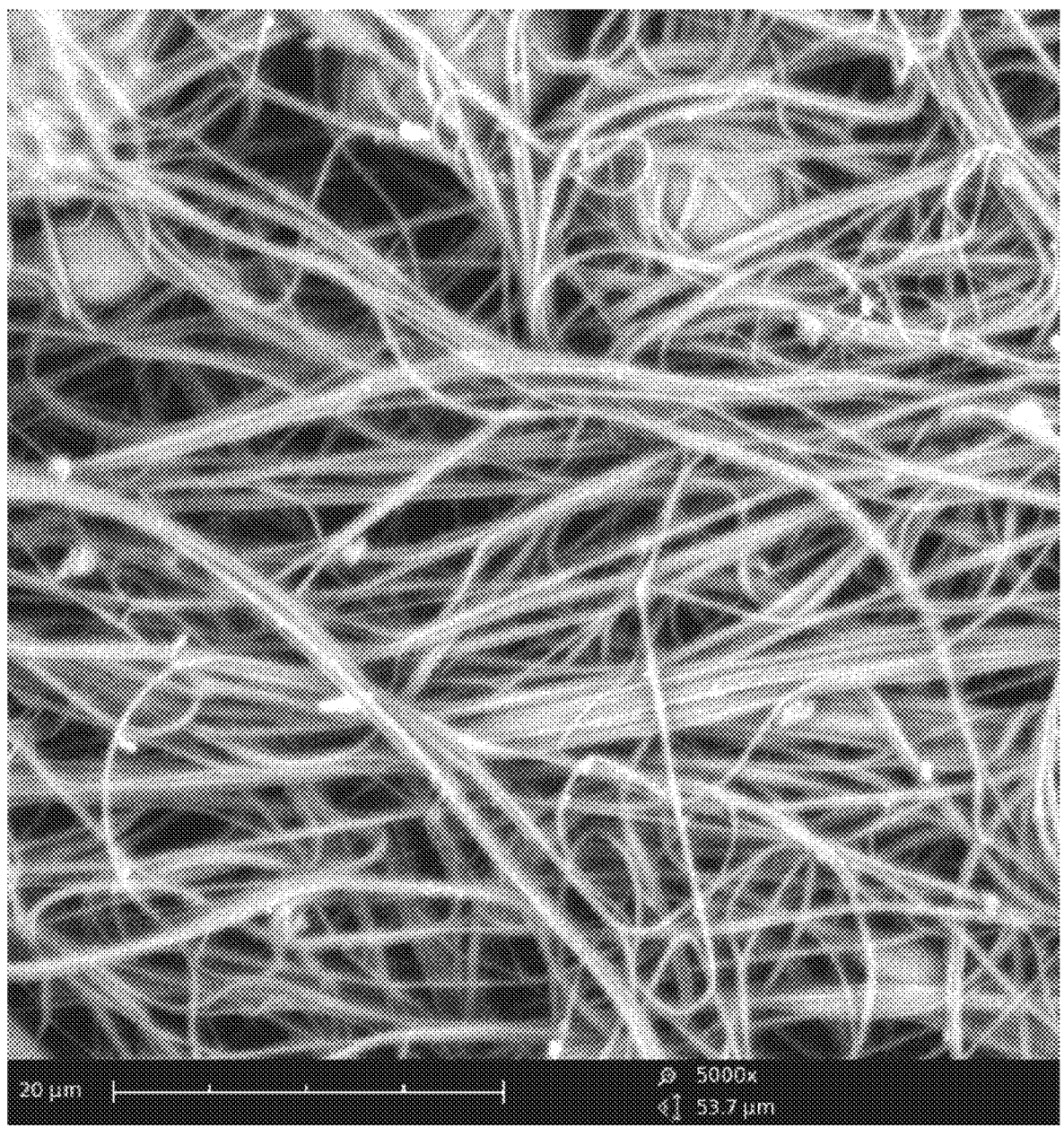
Figure 3C:
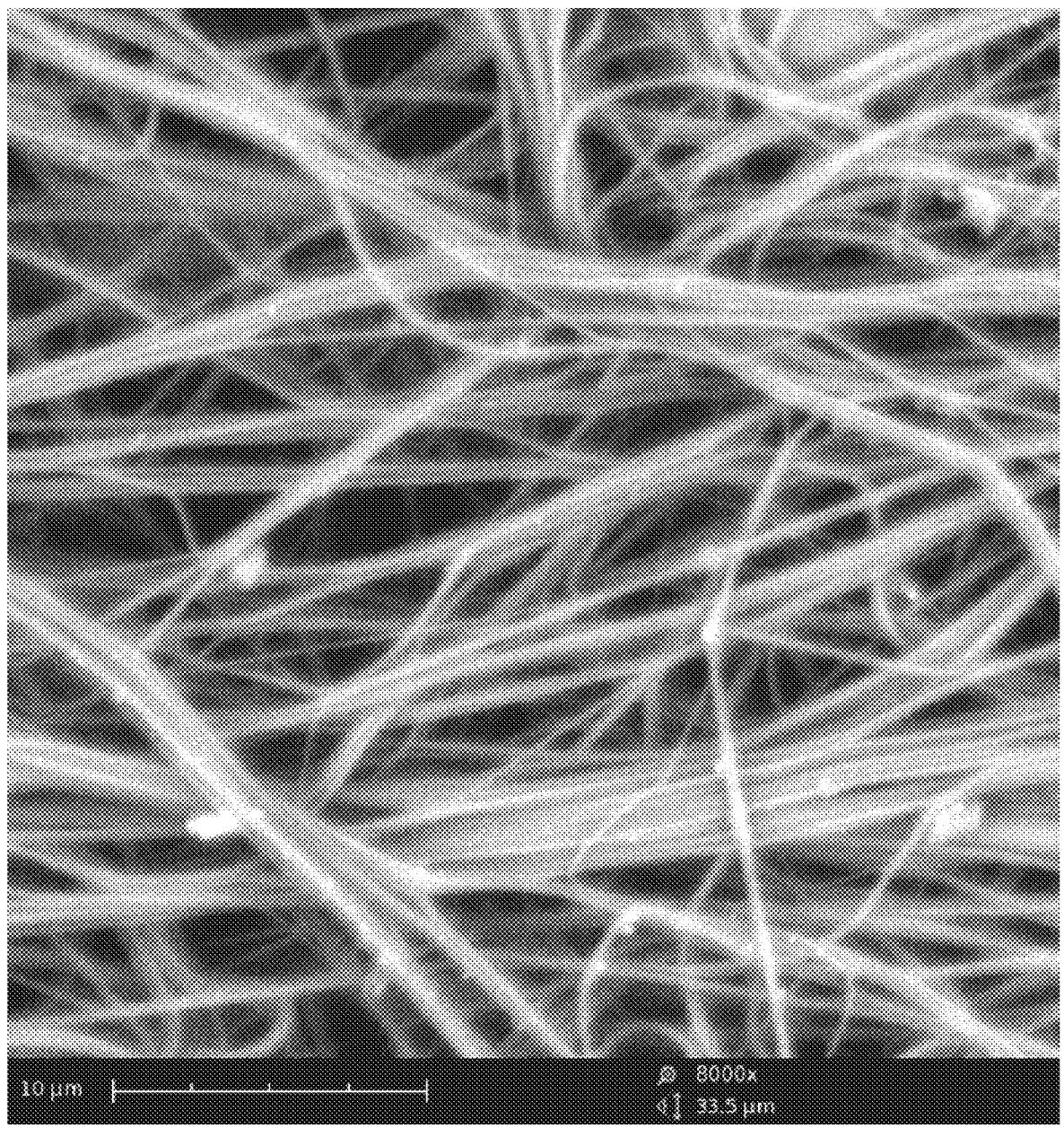
Figure 3D:
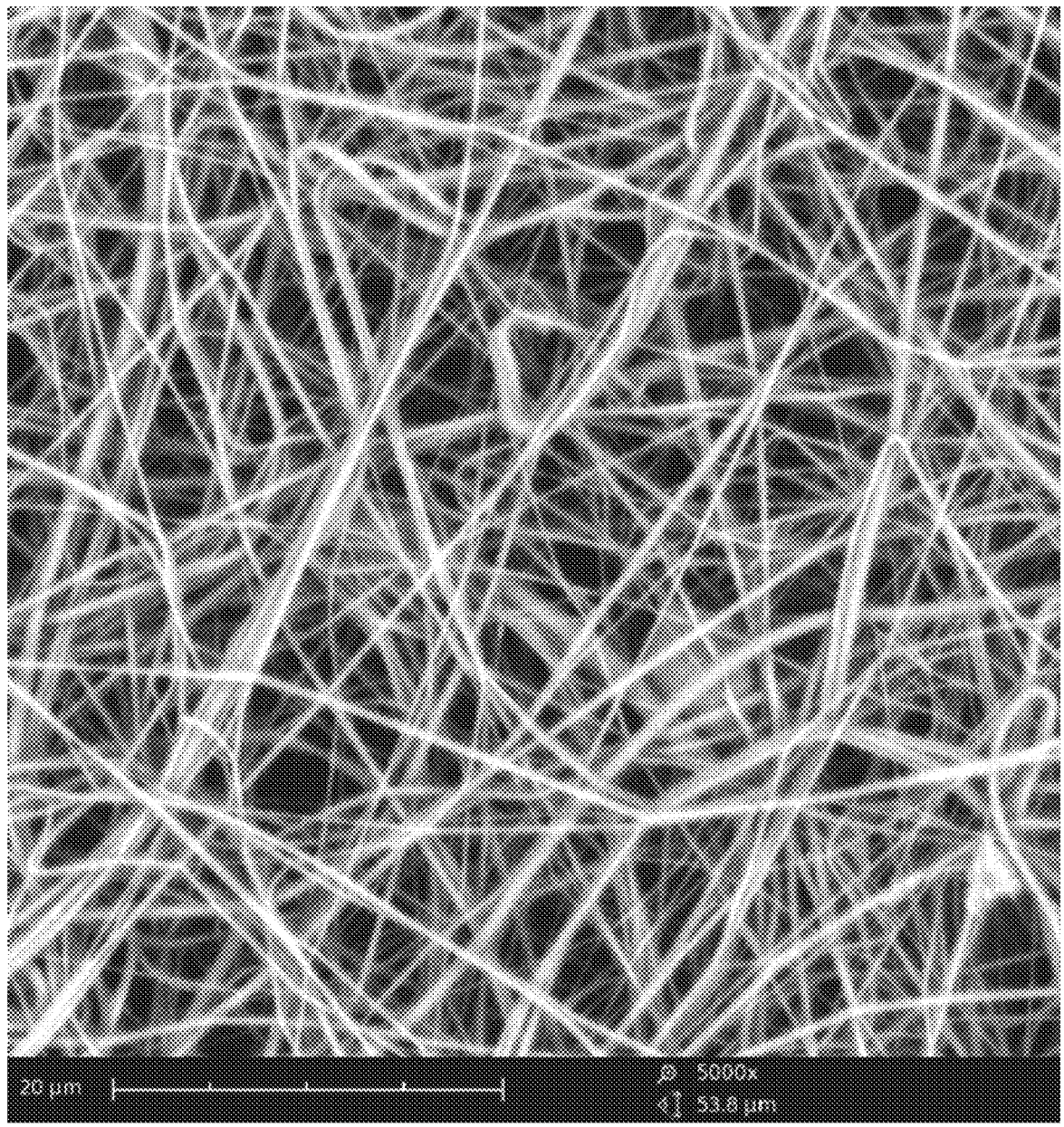
Figure 3E:
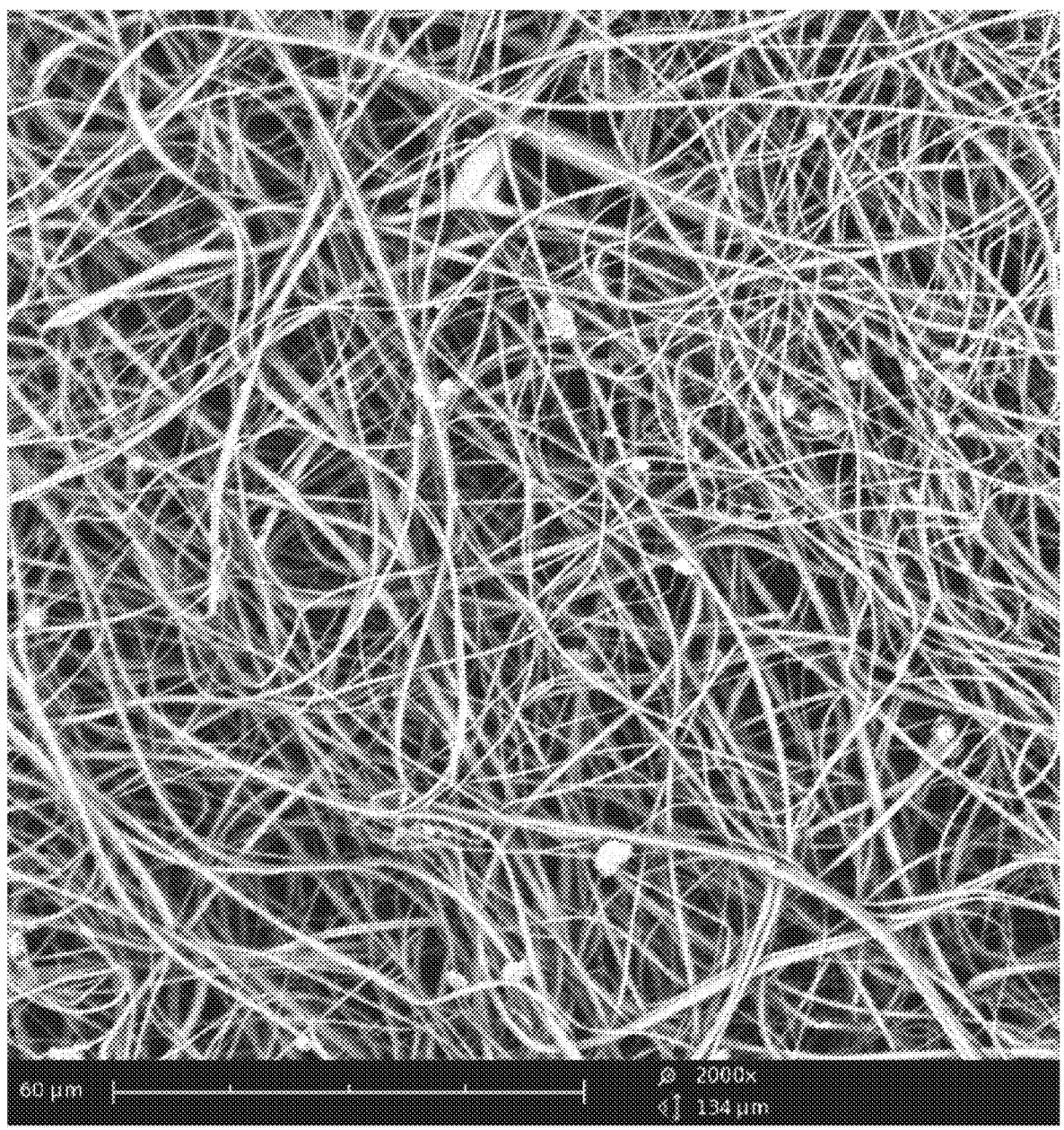
Figure 3F:
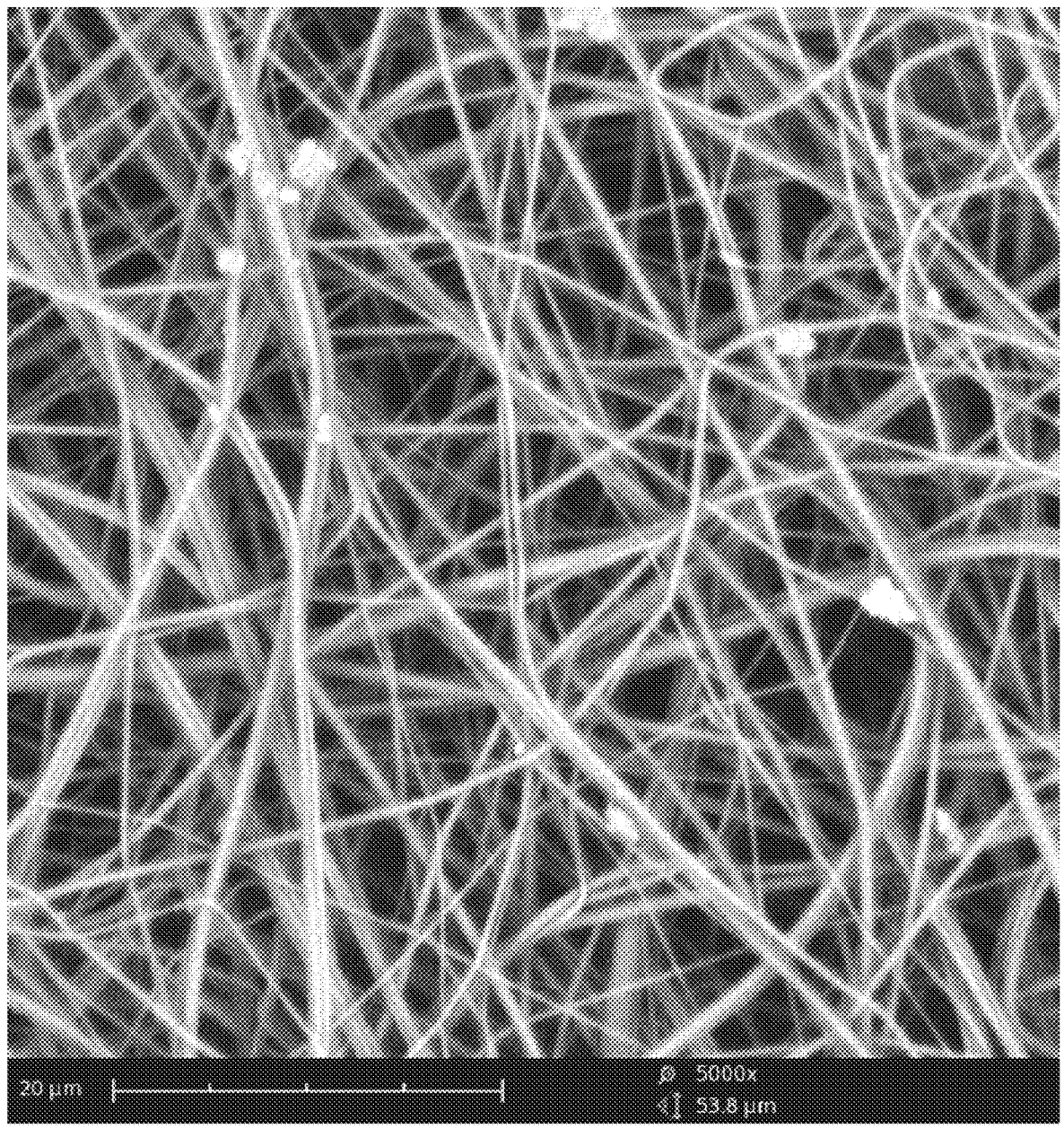
Figure 3G:
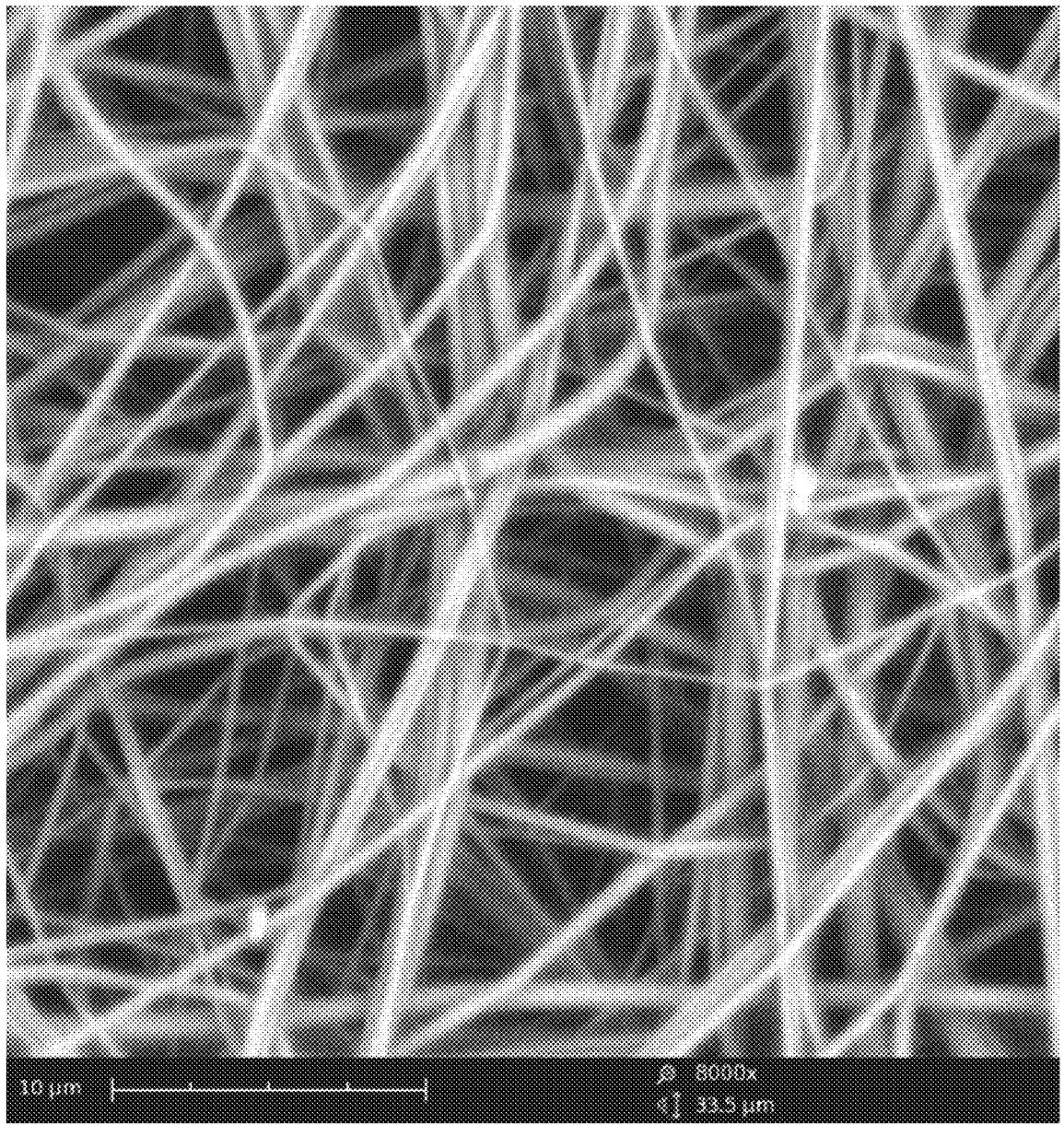
Figure 3H:
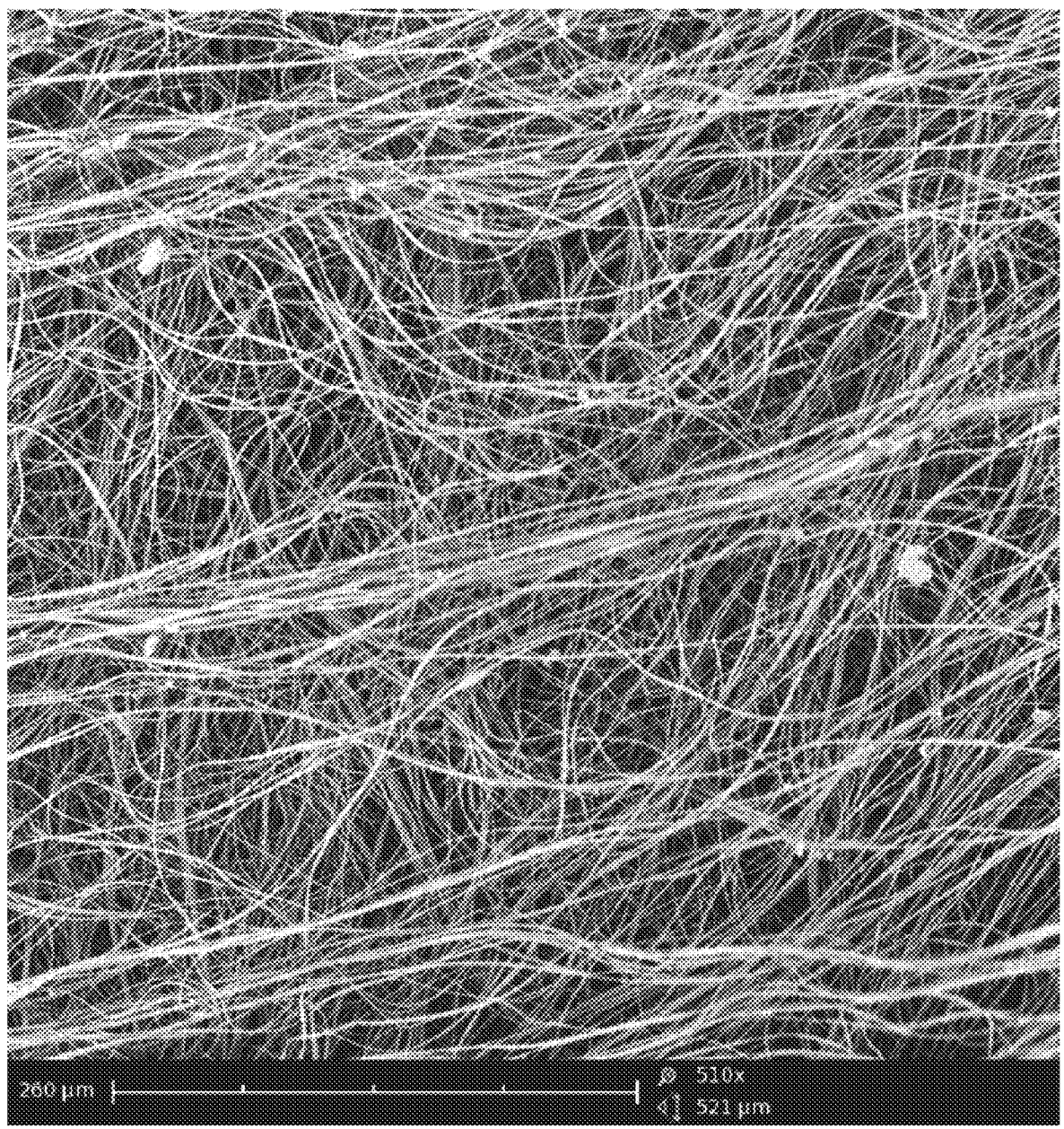
Figure 3I:
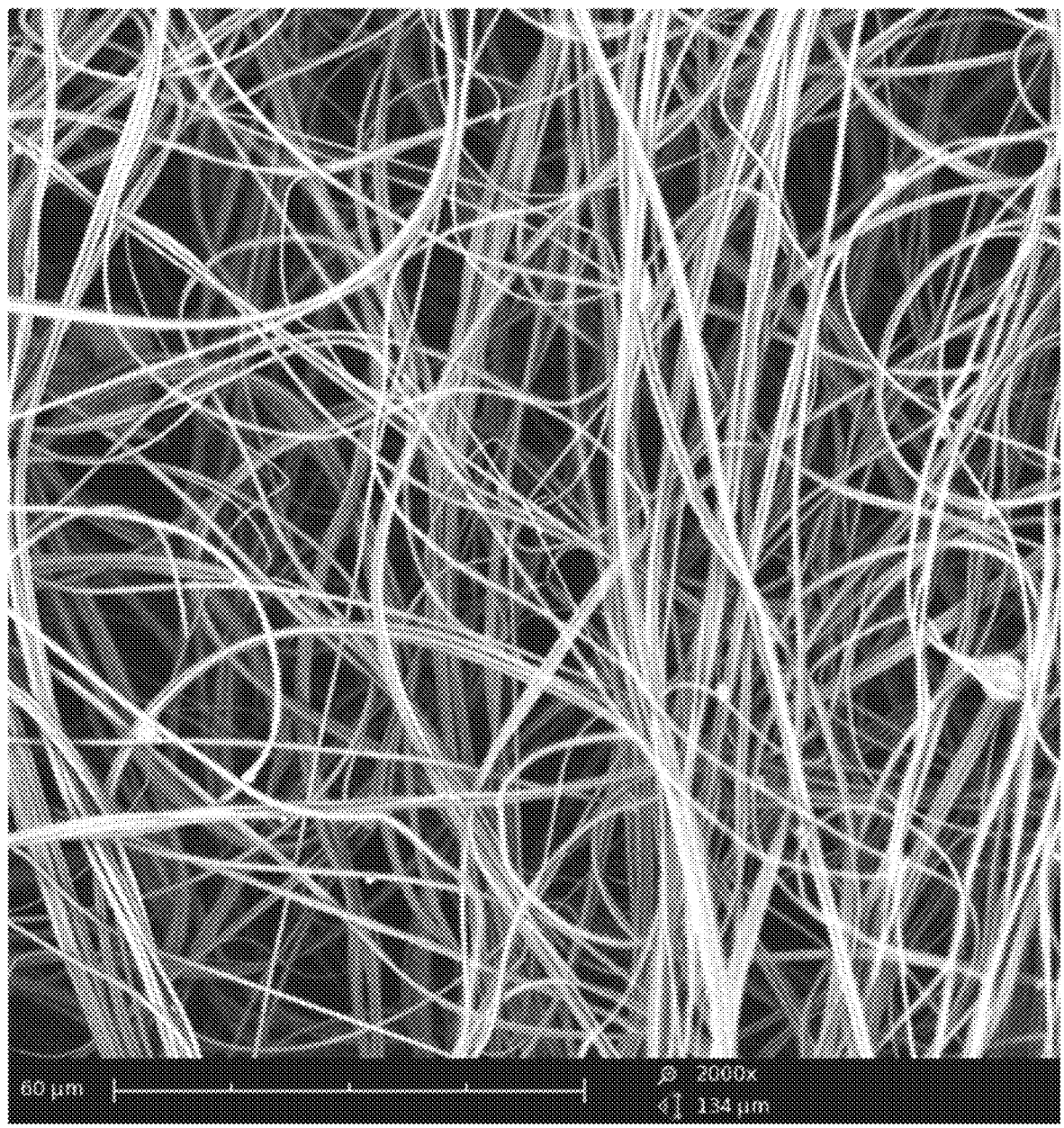
Figure 3J:
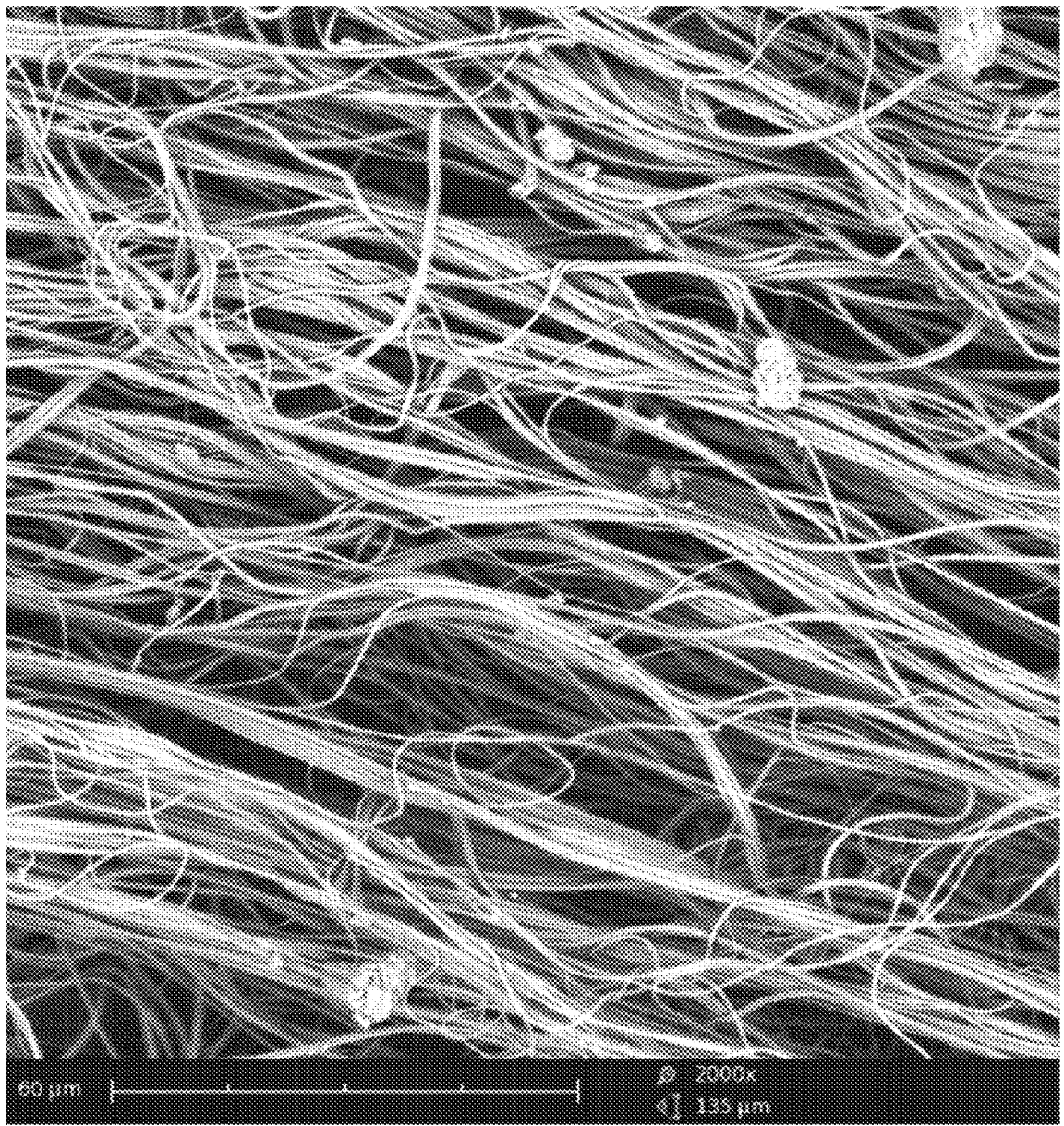
Figure 3K:
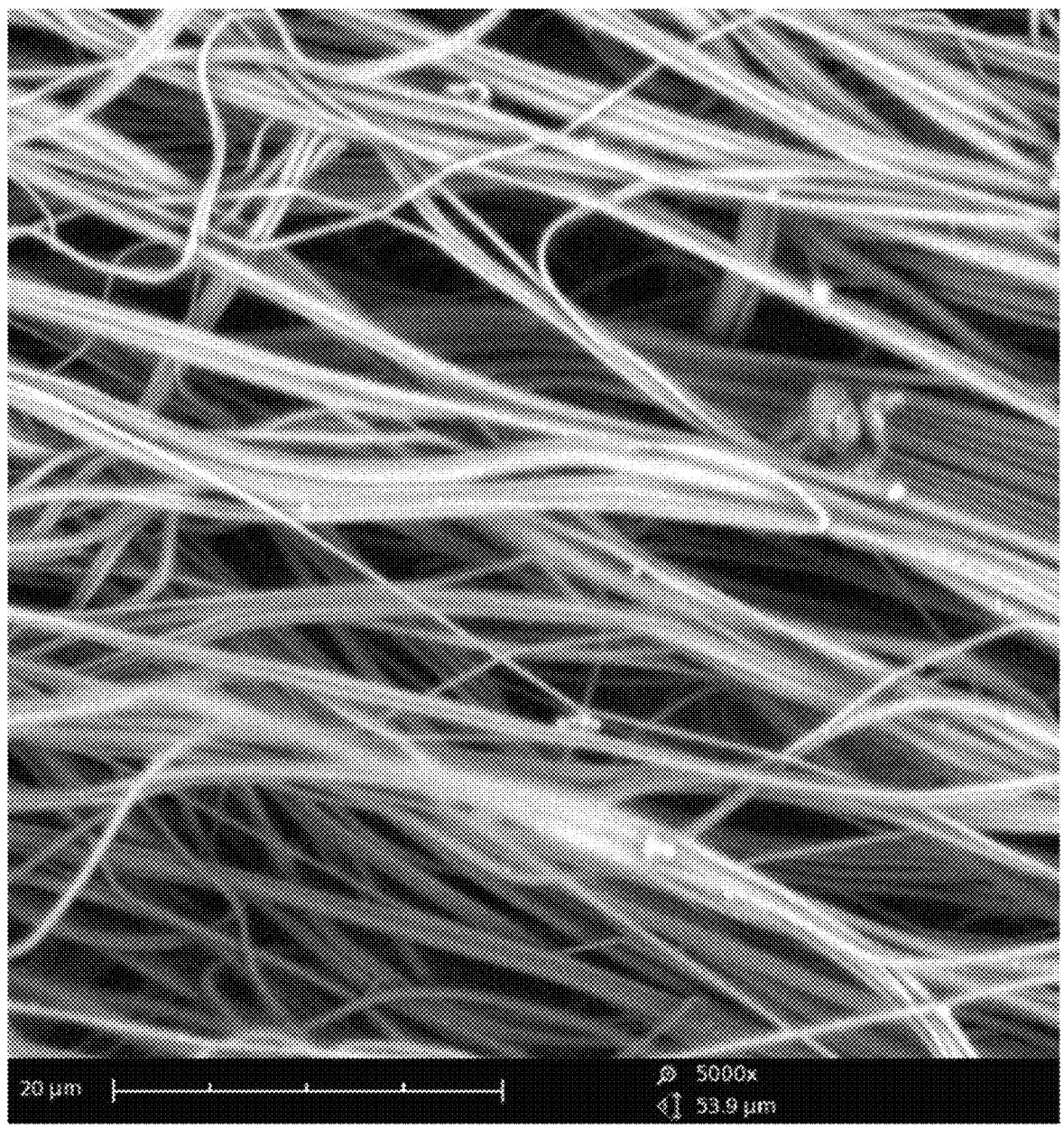

FIGS. 3a, 3b, 3c, 3d, 3e, 3f, 3g, 3h, 3i, 3j, and 3k. Scanning electron micrograph images of successfully spun fibers from the L-1000 machine. FIGS. 3a, 3b, and 3c, show Formula 15 fibers. FIG. 3a shows superfine chitosan fibers and large bead defects spun from Formulation 15 at ×2000 magnification. Bead defects result from inhomogeneity in the solution which has been spun or some variability in the spinning. Bead defects are acceptable if they make up a small mass percentage (less than 10% w/w is preferred) of material being spun. FIG. 3b provides a higher magnification image ×5000 of chitosan fibers from Formula 15. FIG. 3c provides a higher magnification image ×8000 of chitosan fibers from Formula 15 and their interstitial pores. FIG. 3d provides an image at ×5000 of chitosan fibers and the nonwoven matrix structure from Formula 16. FIGS. 3e, 3f, and 3g, show Formula 17 fibers. FIG. 3e shows superfine chitosan fibers spun from Formulation 17 at ×2000 magnification. FIG. 3f provides a higher magnification image ×5000 of chitosan fibers from Formula 17. FIG. 3g provides a higher magnification image ×8000 of chitosan fibers, the fiber matrix and its pores from Formula 17. FIGS. 3h and 3i show Formulation 20 fibers. FIG. 3h shows superfine chitosan fibers spun from Formulation 20 at ×510 magnification. FIG. 3i provides a higher magnification image ×2000 of chitosan fibers from Formula 20. FIGS. 3j and 3k show Formulation 24 fibers. FIG. 3j shows superfine chitosan fibers and bead defects spun from Formulation 24 at ×2000 magnification. FIG. 3k provides a higher magnification image ×5000 of chitosan fibers, their matrix structure and pores from Formula 24.

Figure 4A:
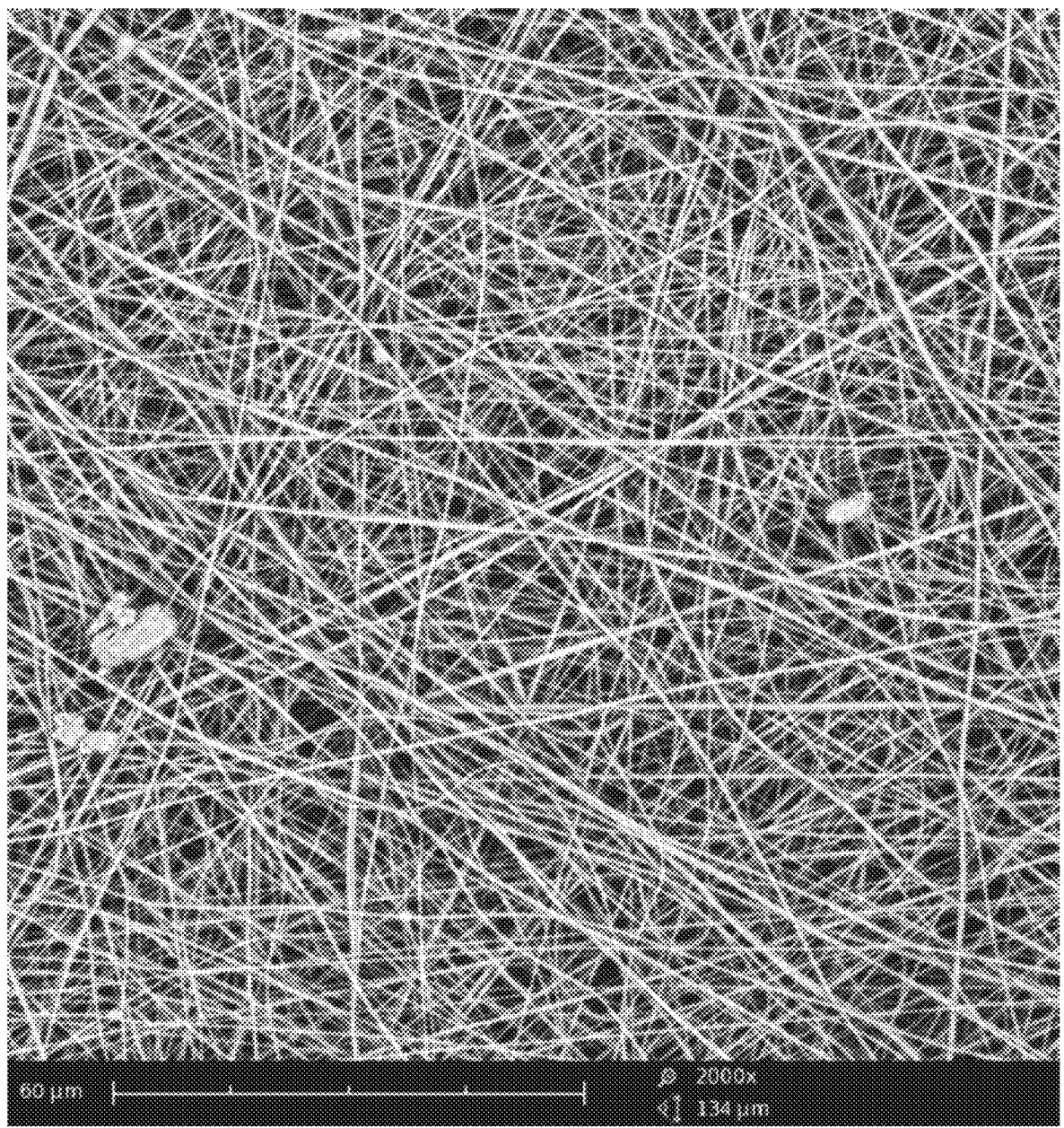
Figure 4B:
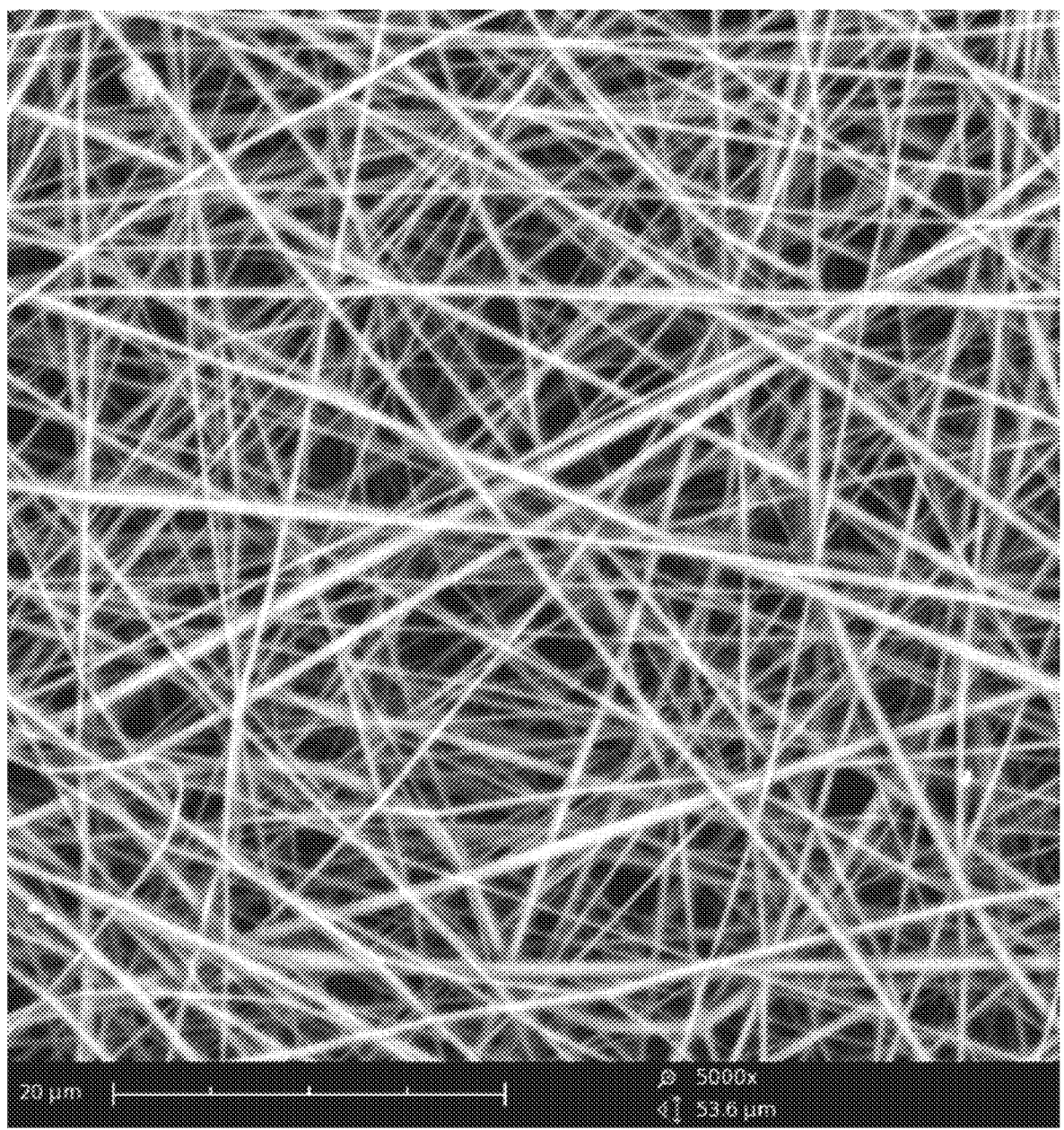
Figure 4C:
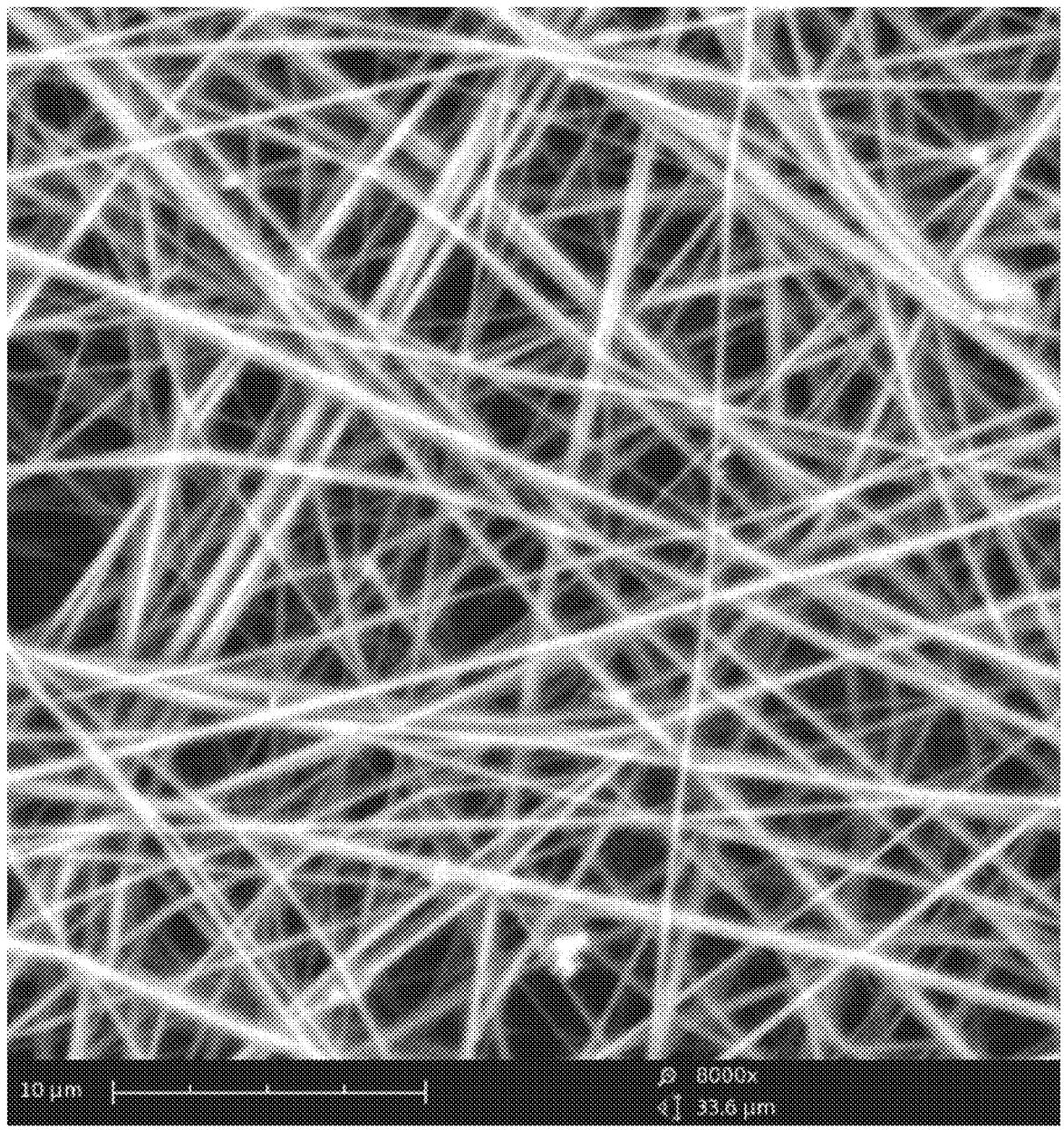
Figure 4D:
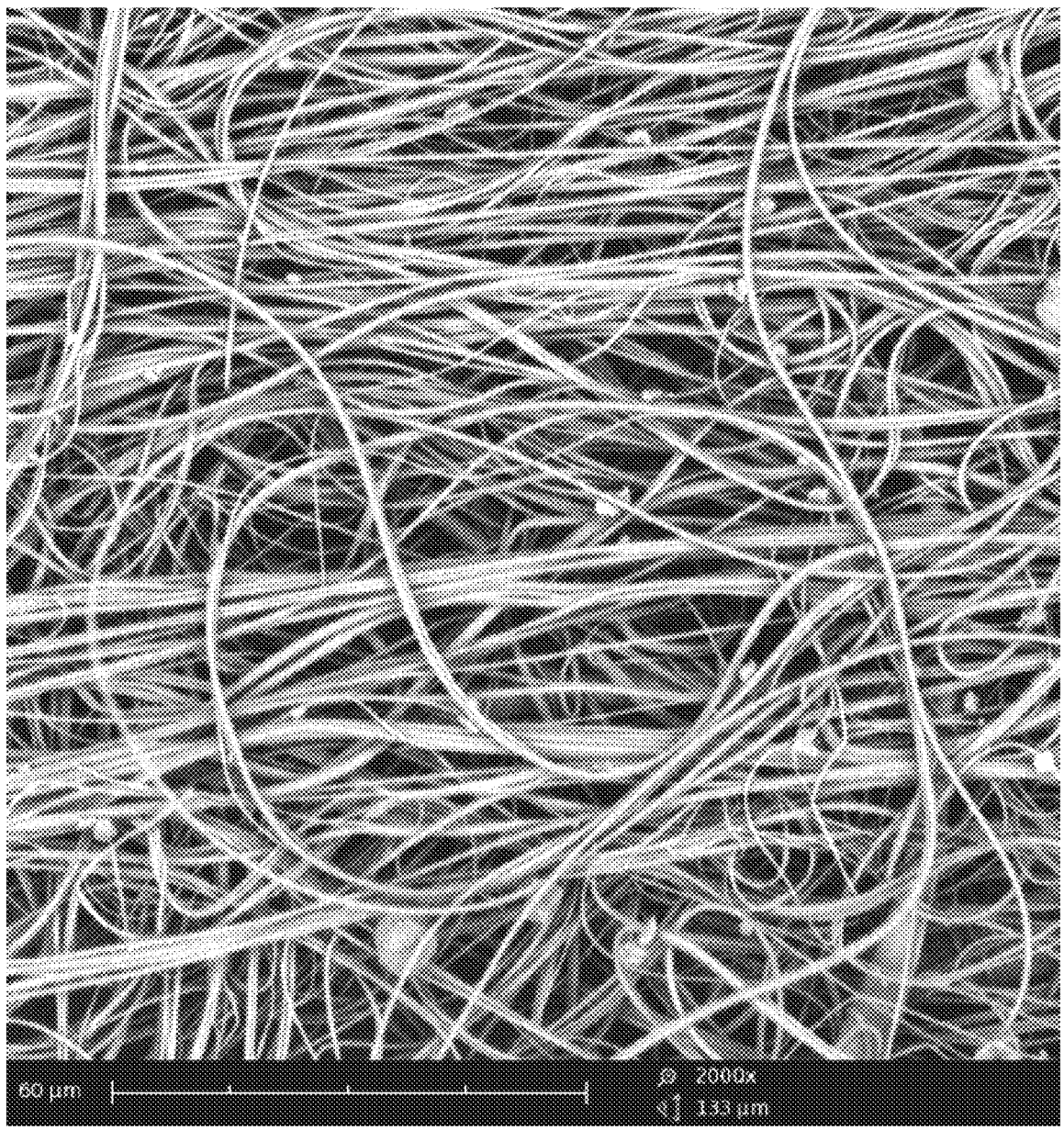
Figure 4E:
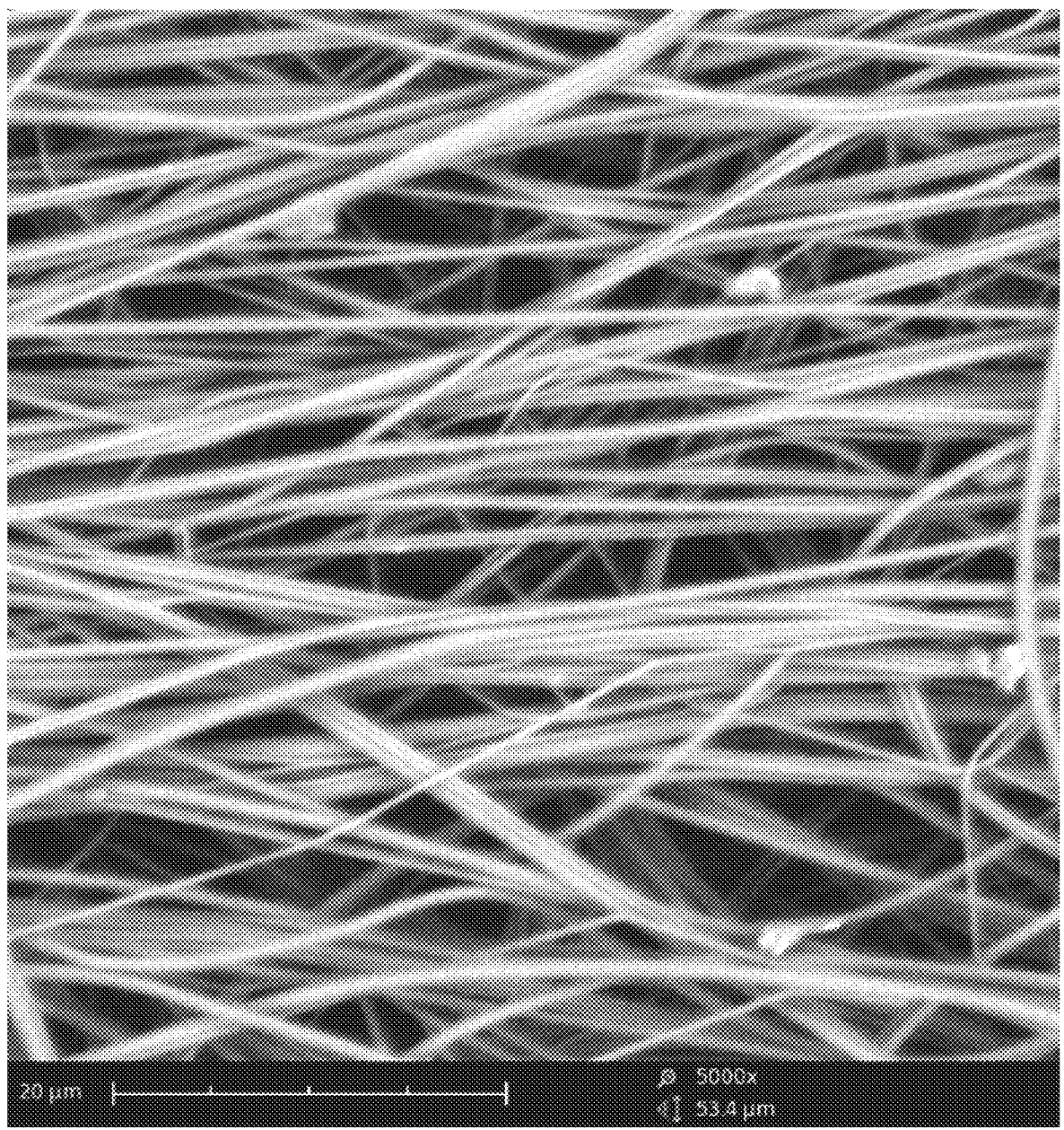
Figure 4F:
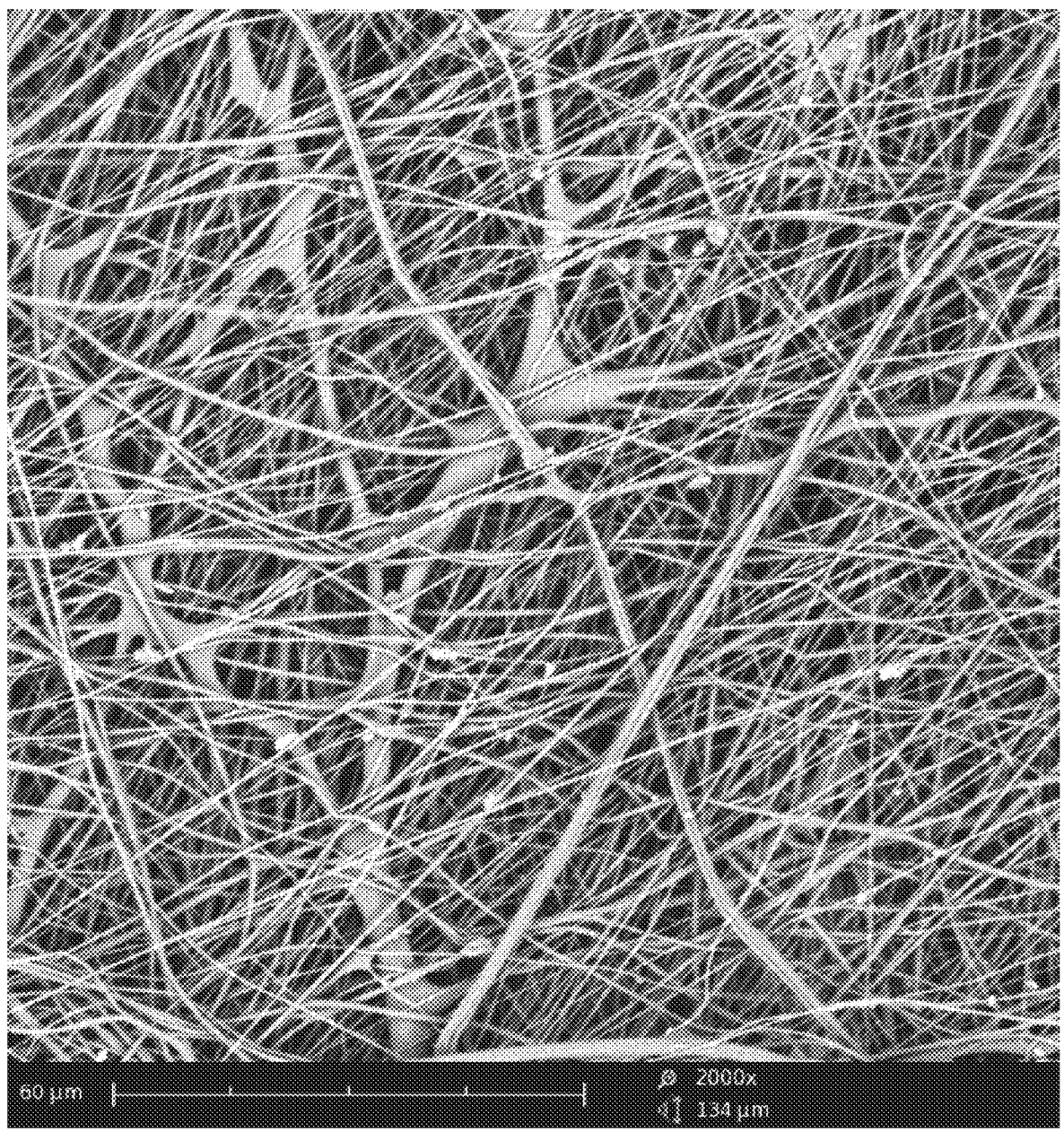
Figure 4G:
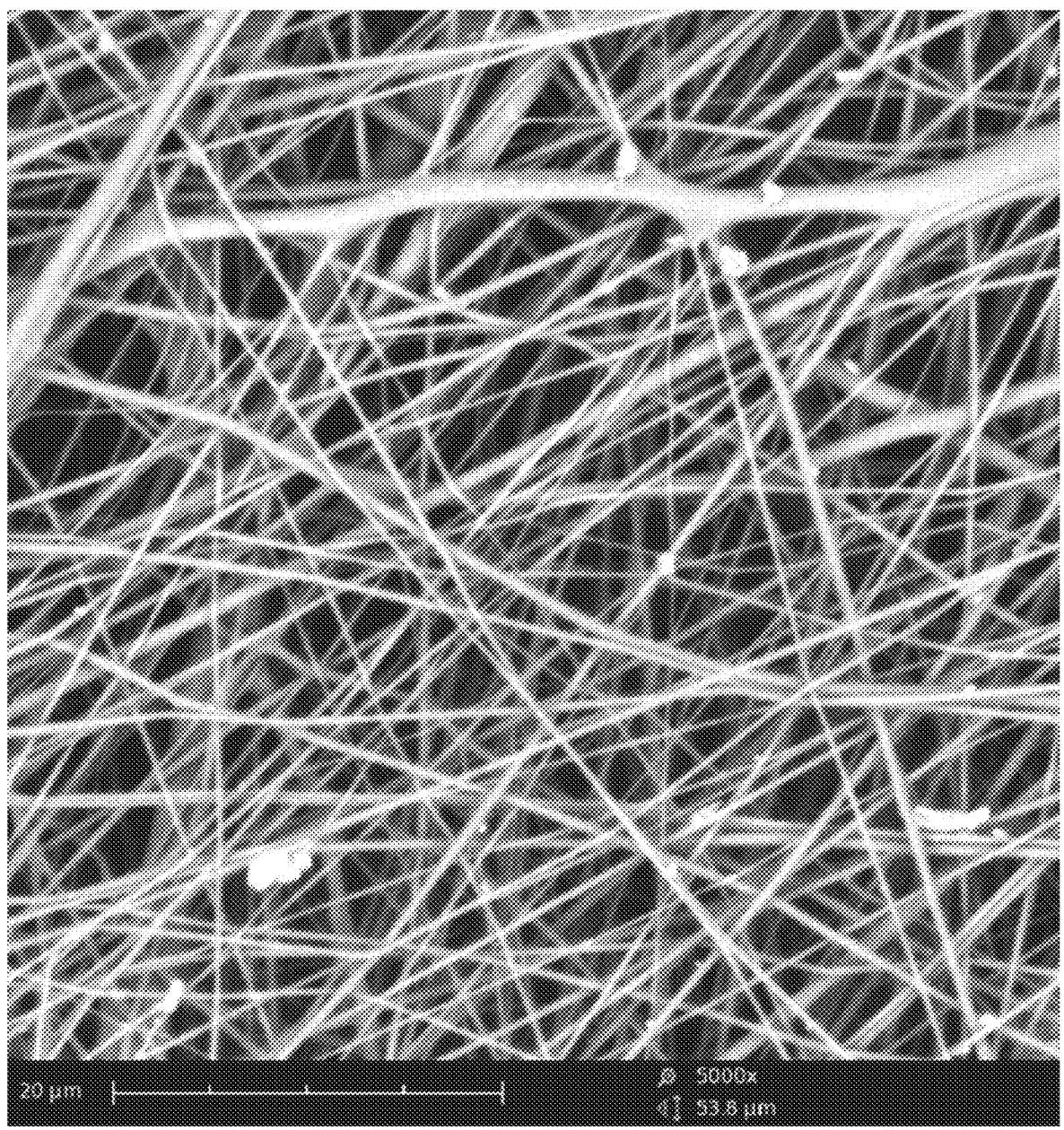
Figure 4H:
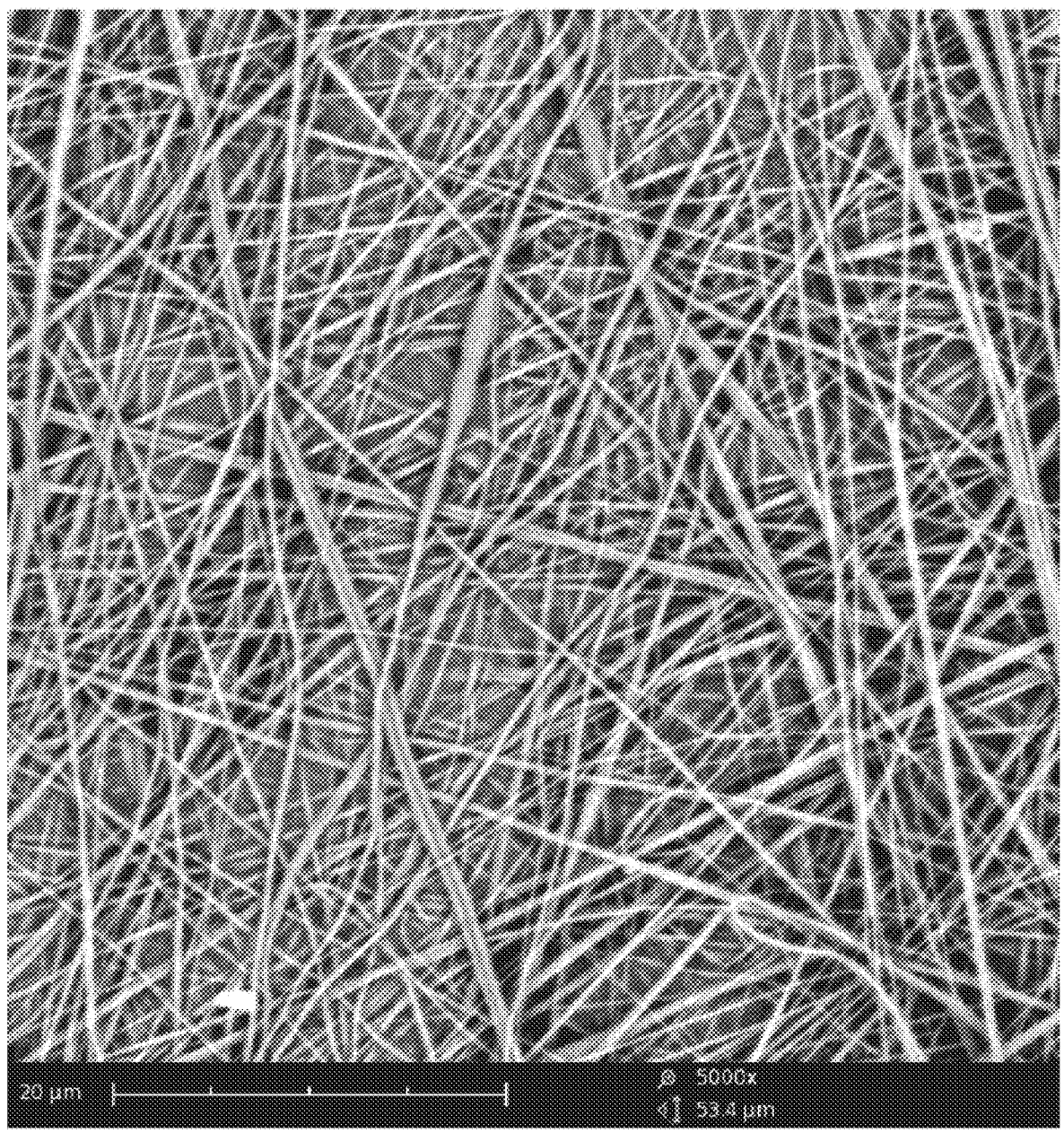
Figure 4I:
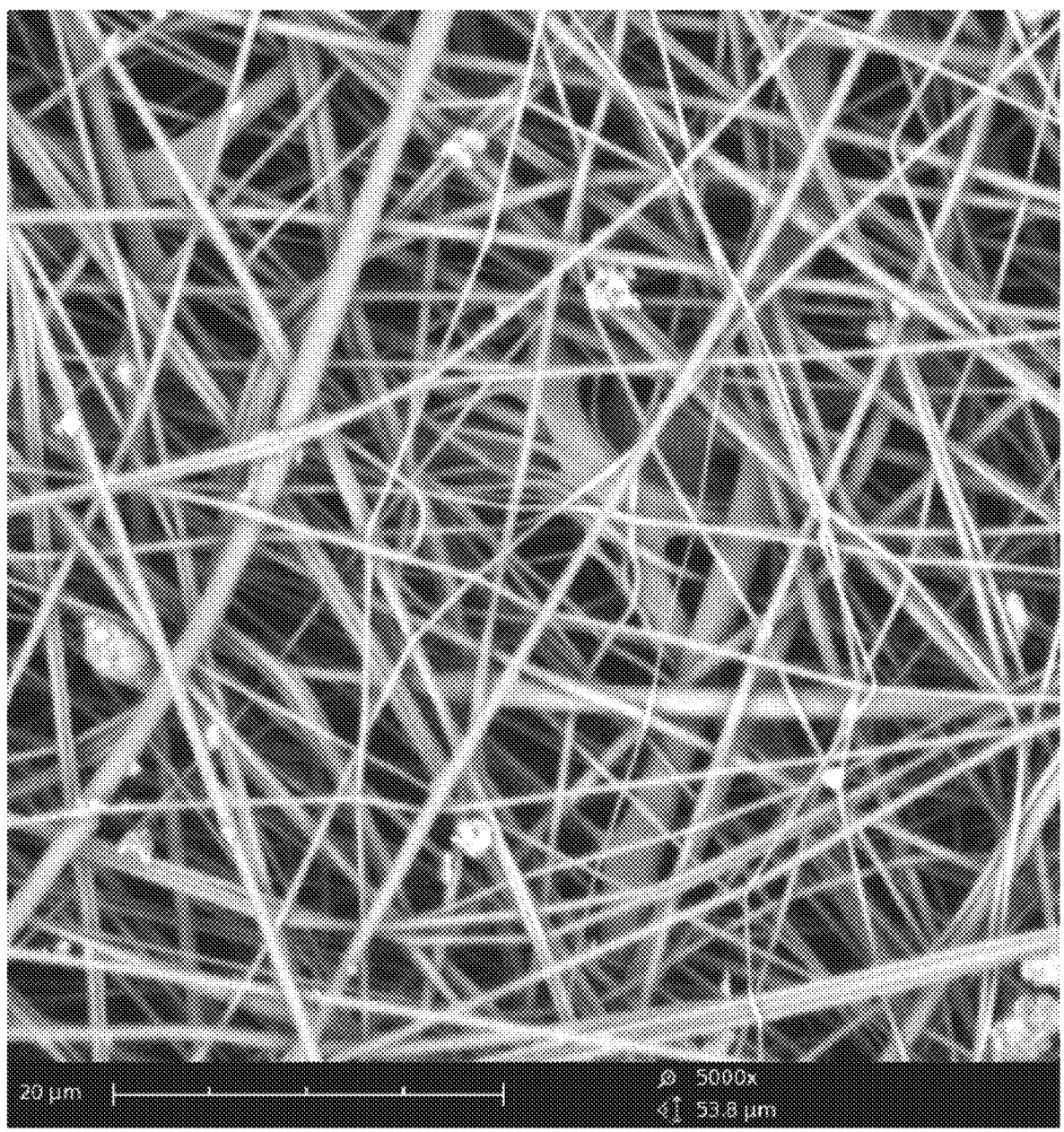
Figure 4J:
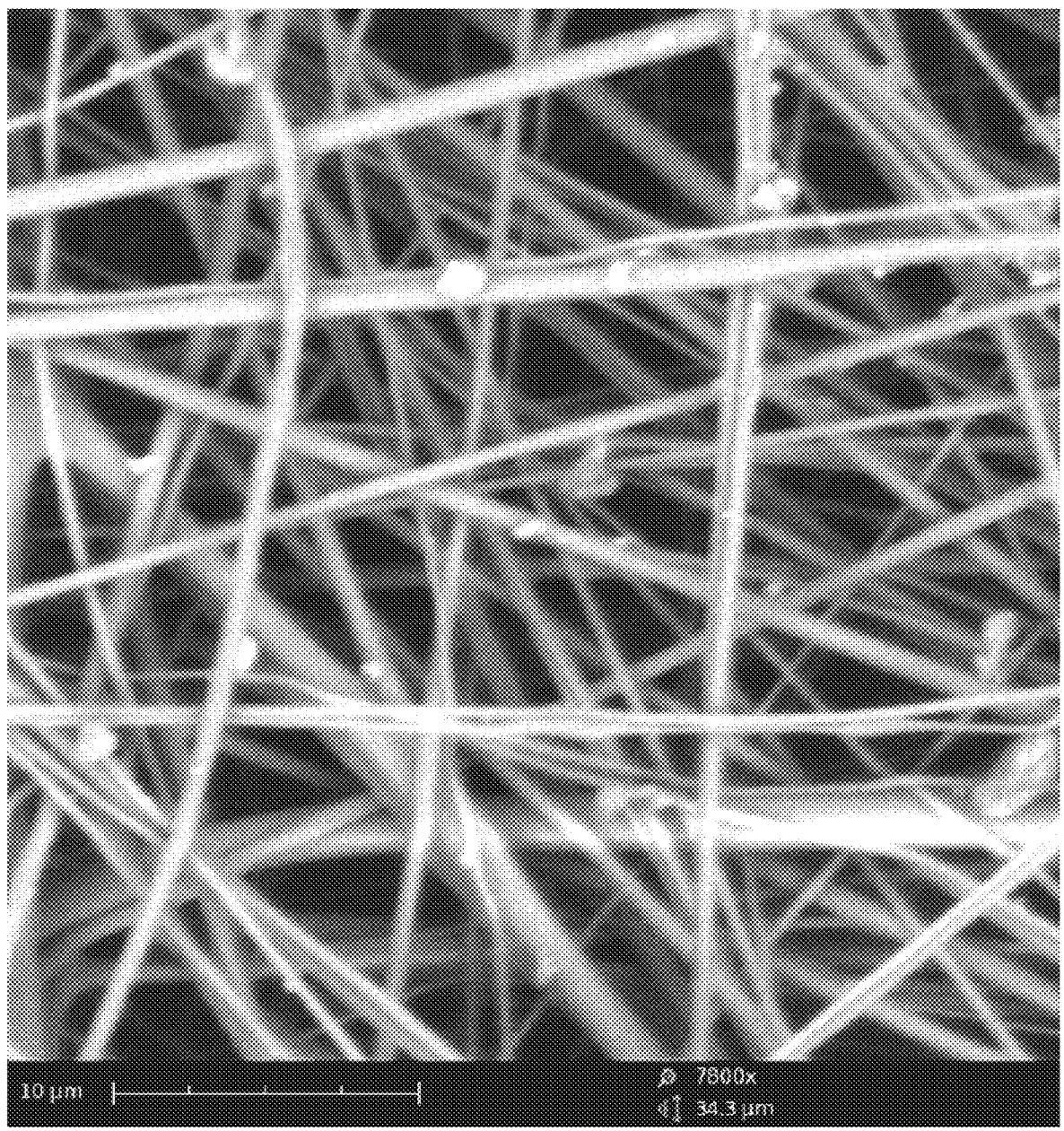
Figure 4K:
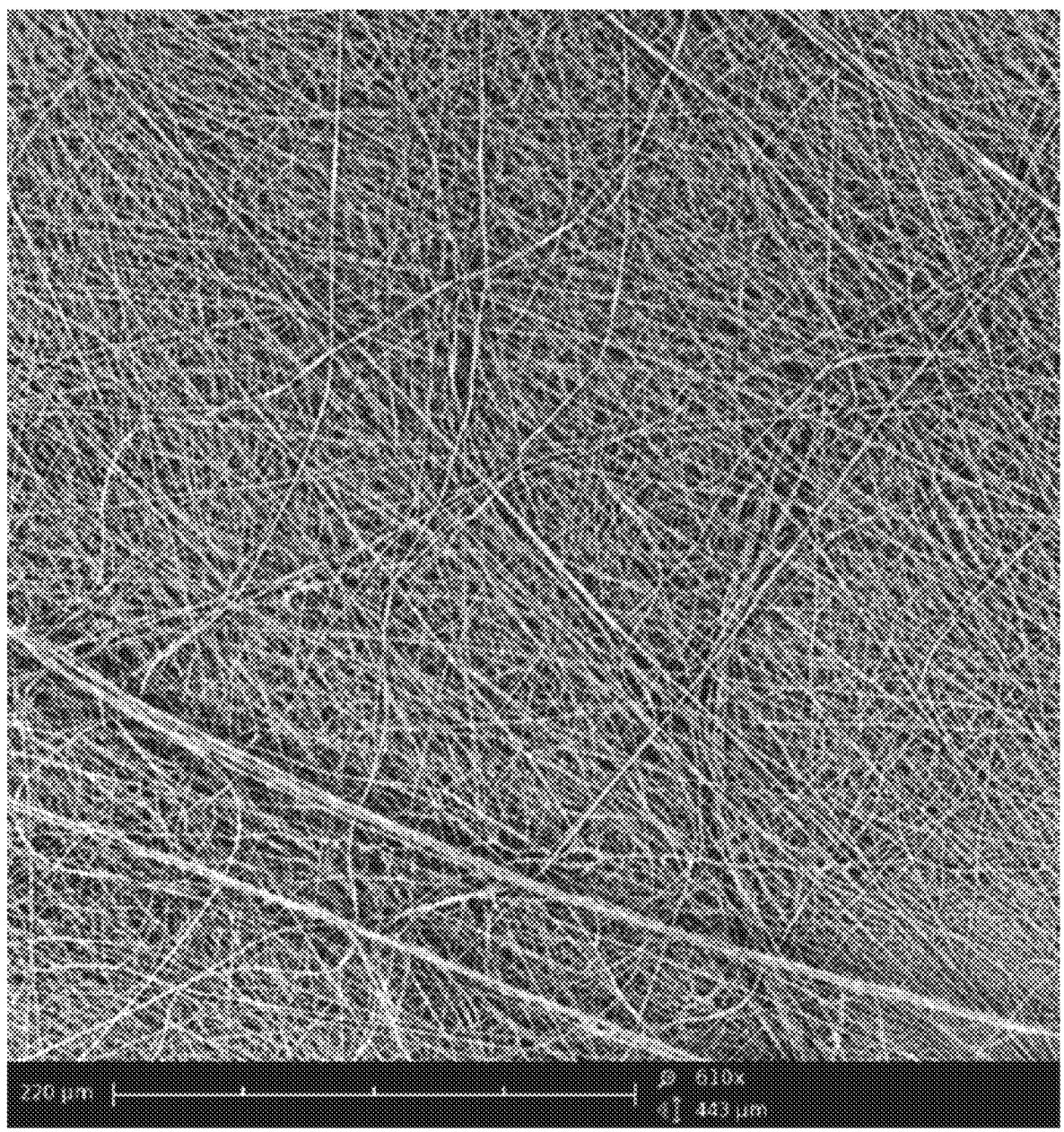
Figure 4L:
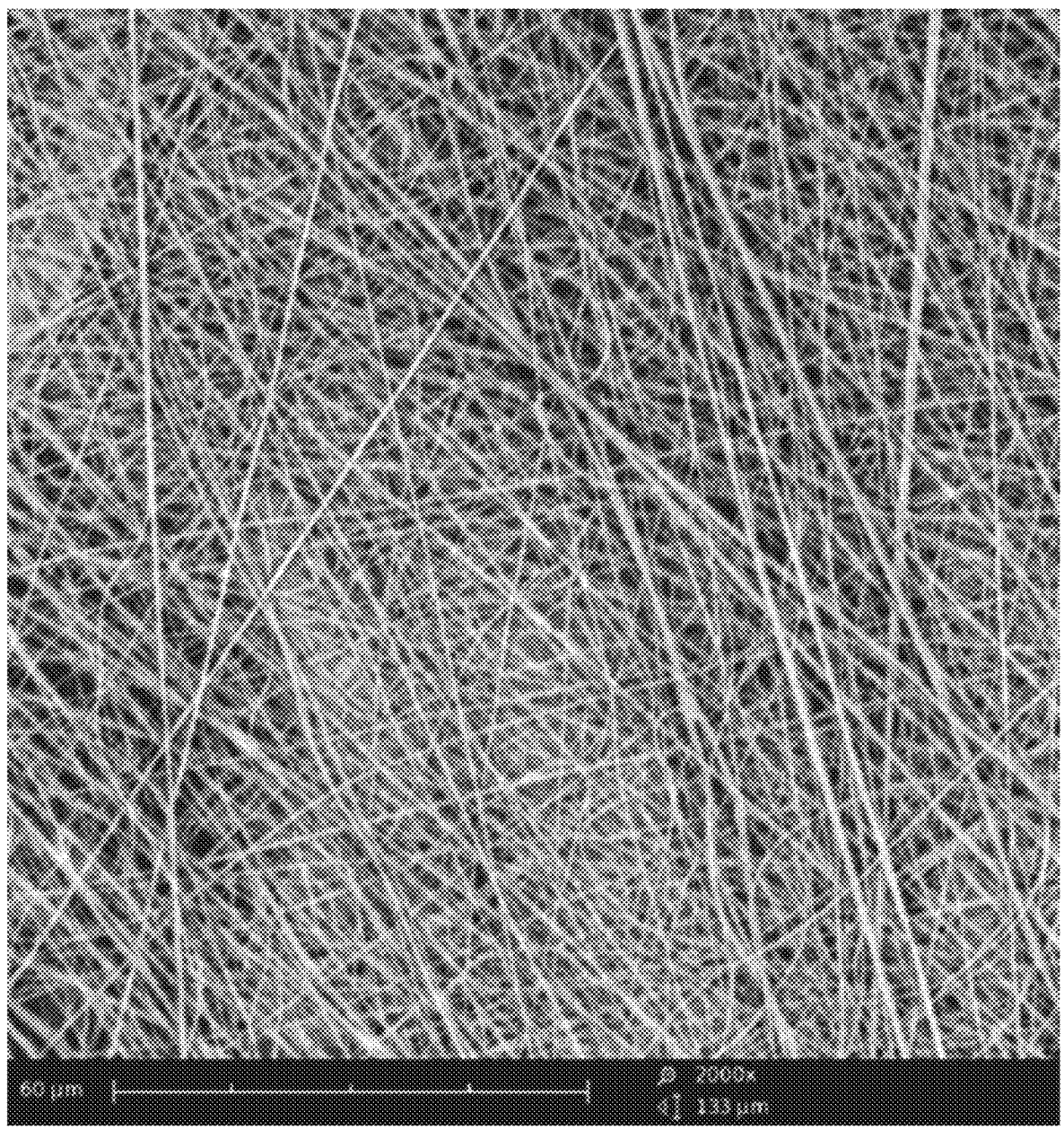
Figure 4M:
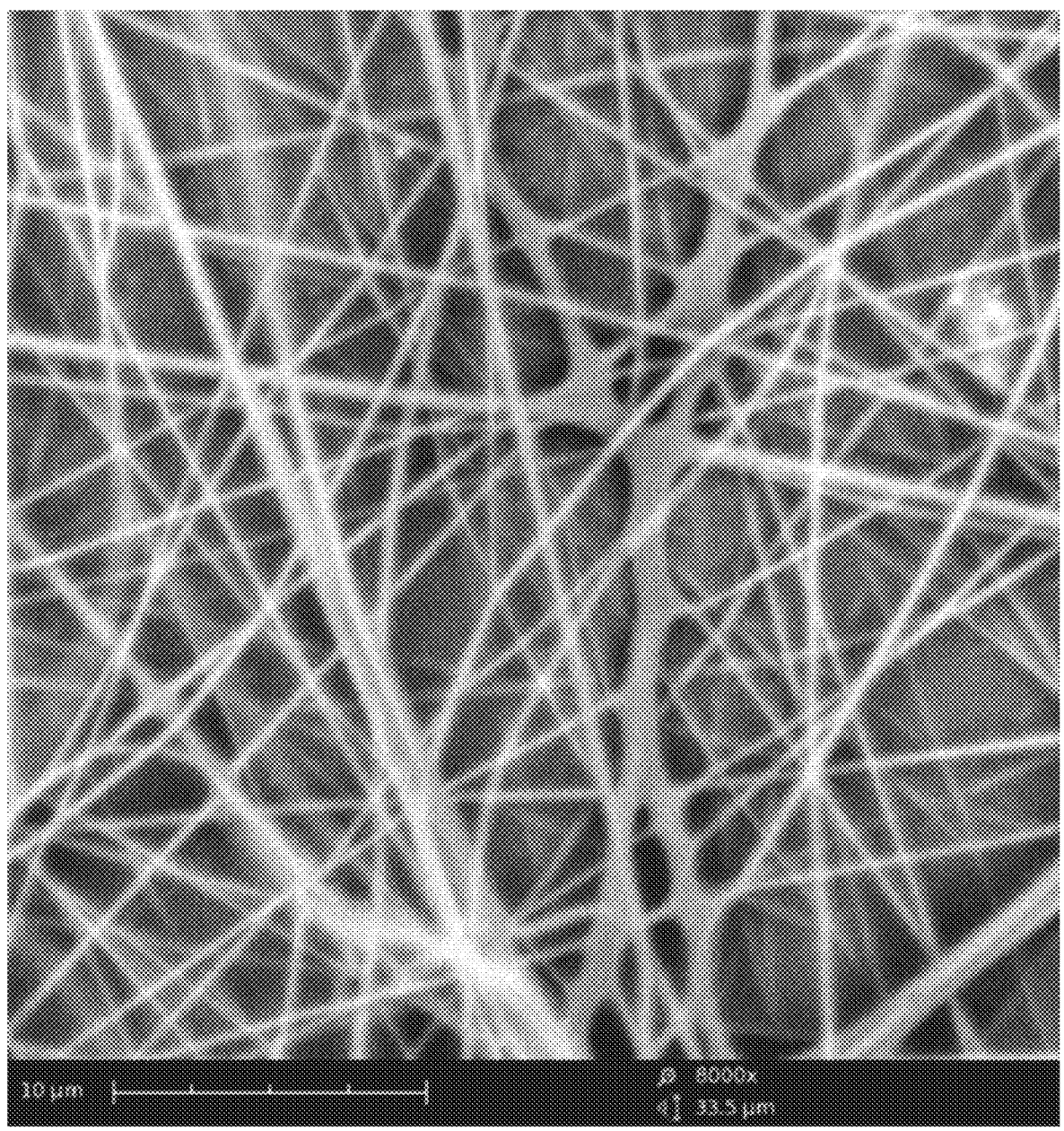

FIGS. 4a, 4b, 4c, 4d, 4e, 4f, 4g, 4h, 4i, 4j, 4k, 4l, and 4m. Scanning electron micrograph images of successfully spun fibers from the FE1.1 machine. FIGS. 4a, 4b and 4c show superfine chitosan fibers spun from Formulation 25. FIG. 4a shows superfine chitosan fibers spun from Formulation 25 at ×2000 magnification. FIG. 4b provides a higher magnification image ×5000 of chitosan fibers, the fiber matrix and its pores from Formulation 25. FIG. 4c provides a higher magnification image ×8000 of chitosan fibers, the fiber matrix and its pores from Formulation 25. FIGS. 4d, 4e, 4f and 4g, show superfine chitosan fibers spun from Formulation 26. FIG. 4d shows superfine chitosan fibers and bead defects spun from Formulation 26 at ×2000 magnification. FIG. 4e provides a higher magnification image ×5000 of chitosan fibers, the fiber matrix and its pores from Formula 26. FIG. 4f shows superfine chitosan fibers and tree-like structure spun from Formulation 26 at ×2000 magnification. FIG. 4g provides a higher magnification image ×5000 of the tree-like structure, the chitosan fibers, the fiber matrix and its pores from Formulation 26. FIG. 4h provides a high magnification image ×5000 of the chitosan fibers, the fiber matrix and its pores from Formulation 27. FIGS. 4i and 4j show superfine chitosan fibers spun from Formulation 28. FIG. 4i provides a high magnification image ×5000 of chitosan fibers, the fiber matrix and its pores from Formulation 28. FIG. 4j provides a higher magnification image ×7800 of chitosan fibers, the fiber matrix and its pores from Formulation 28. FIGS. 4k, 4l, and 4m show superfine chitosan fibers spun from Formulation 29. FIG. 4k demonstrates superfine chitosan fibers spun from Formulation 29 at ×610 magnification. FIG. 4l provides a higher magnification image ×2000 of chitosan fibers, the fiber matrix and its pores from Formulation 29. FIG. 4m provides a higher magnification image ×8000 of chitosan fibers, the fiber matrix and its pores from Formulation 29.

Figure 5A:
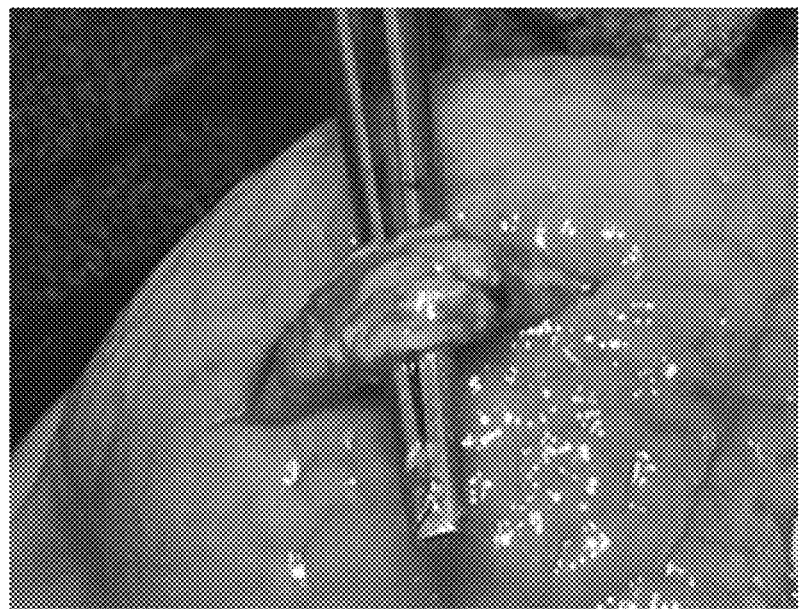
Figure 5B:
Figure 5C:
Figure 5D:
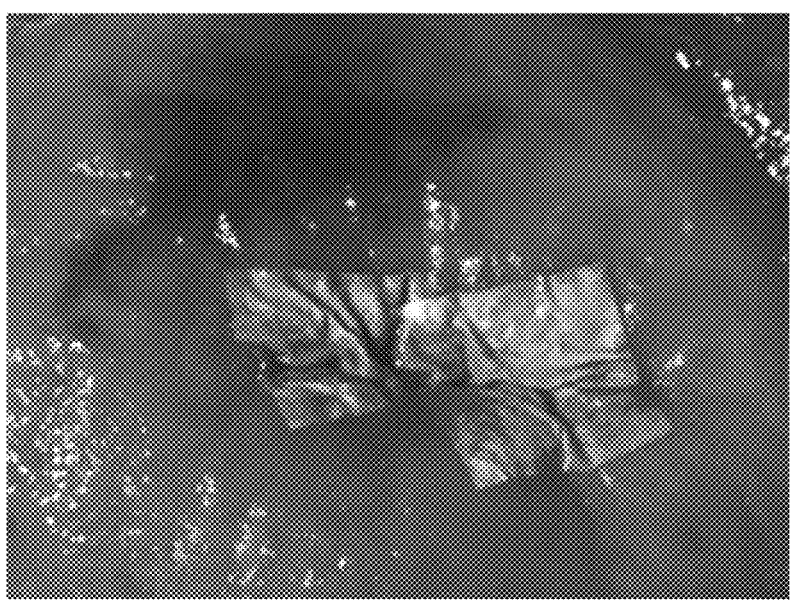
Figure 5E:
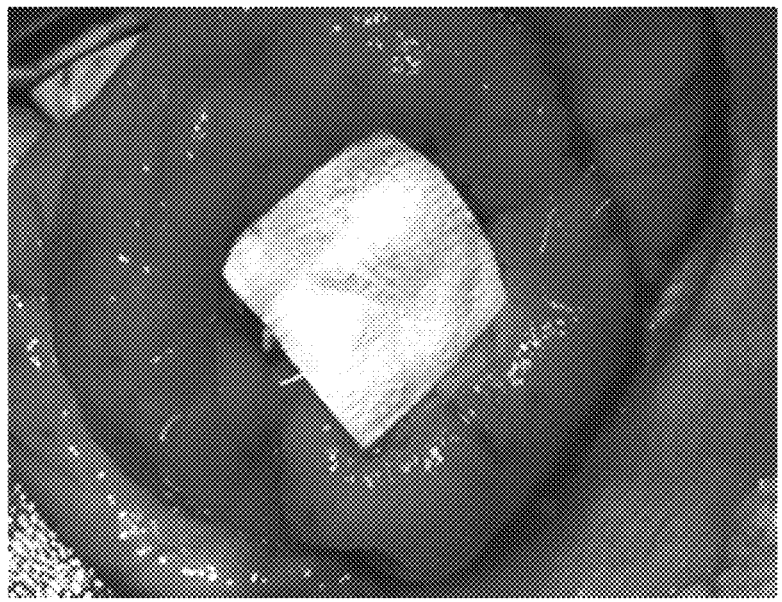
Figure 5F:
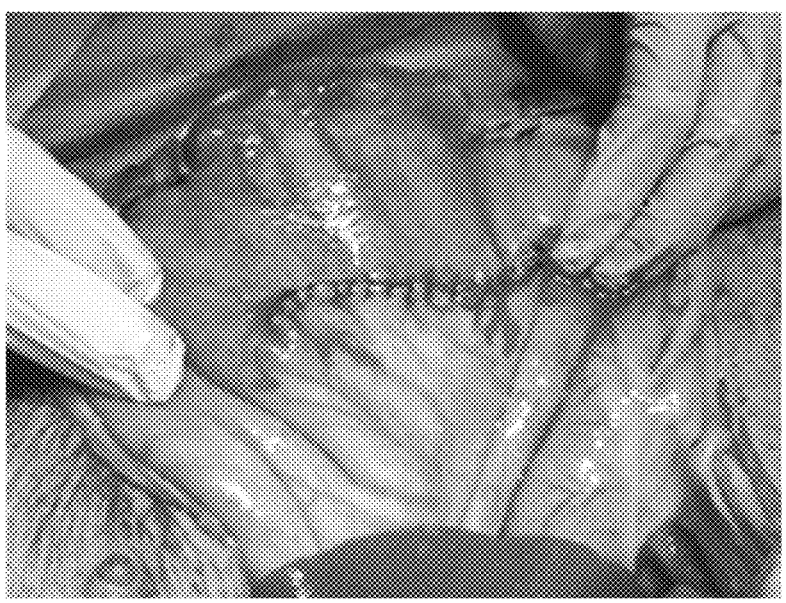
Figure 5G:
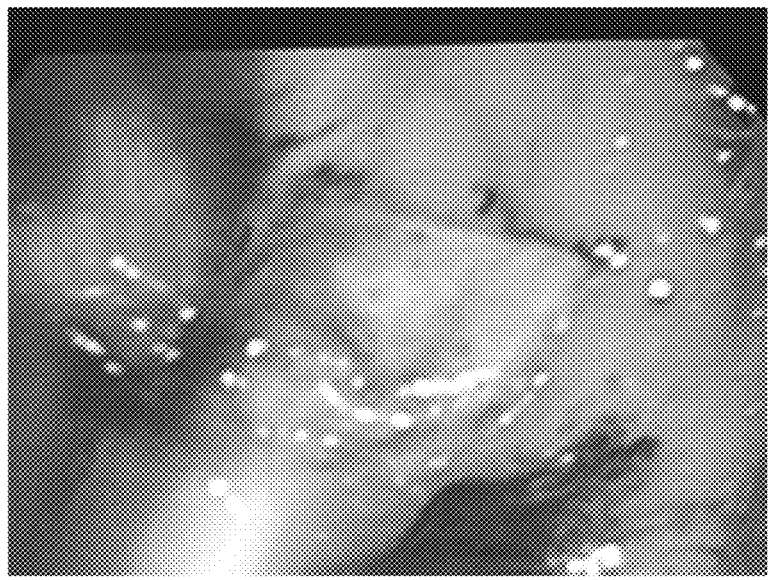
Figure 5H:
Figure 5I:
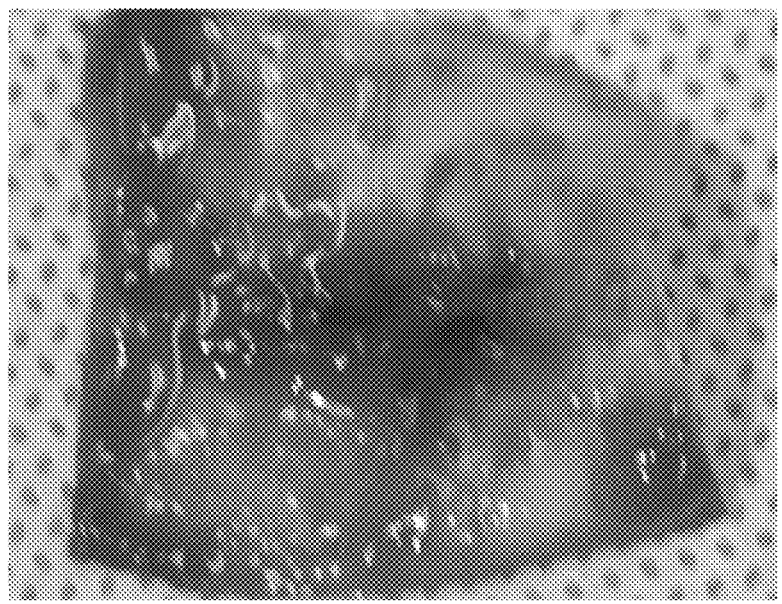
Figure 5J:
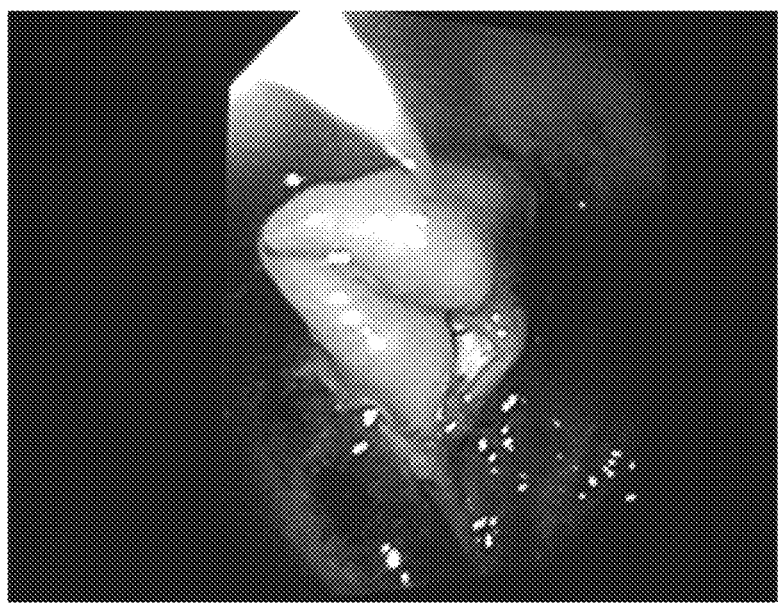
Figure 5K:
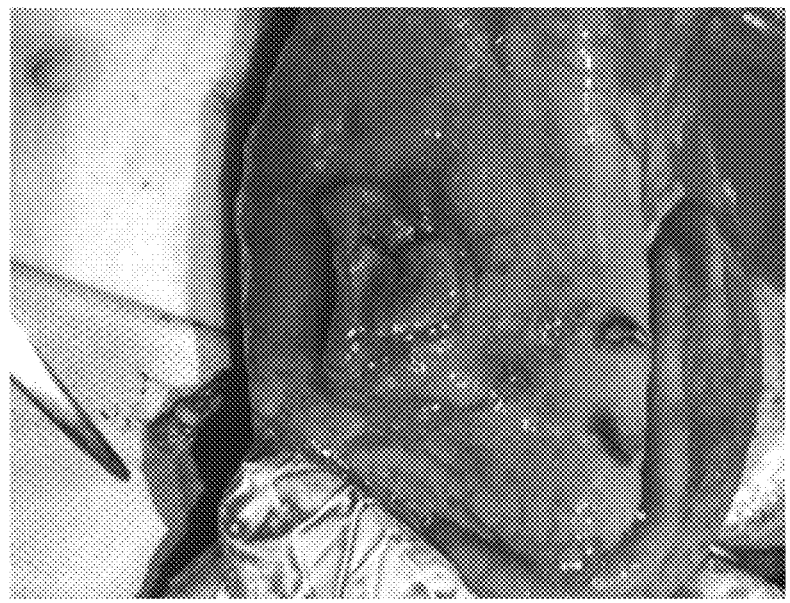

FIGS. 5a, 5b, 5c, 5d, 5e, 5f, 5g, 5h, 5i, and 5k relate to the superfine chitosan fibers and their nonwoven matrices of the invention in applications relating to their wetting properties, their compliance, their conformability to tissue and tissue injuries, their absorption of biological liquid, and their adherence to tissue. These applications are not limited to, but include, delivery of pharmaceutical active ingredients, promotion of local bioactivity in wound care, promotion of local moisture retention, promotion of local wound healing, promotion of local antibacterial activity, and promotion of hemostasis. The superfine chitosan fiber and matrices formed of the superfine fiber may be beneficial in applications including general wound care but may also demonstrate specific suitability for addressing wound care, bleeding, and fluid loss in minimally invasive procedures such as control of upper gastrointestinal bleeding. FIGS. 5a, 5b, 5c, 5d, 5e, 5f, 5g, 5h, 5i, and 5k demonstrate procedures and outcomes in the swine upper gastrointestinal injury study presented in example 3. FIG. 5a shows the inside of the stomach externalized to expose the main artery which has been placed inside the gastric cavity in order to simulate the effect, when injured, of arterial injury bleeding that can result in the life threatening incidence of an eroded stomach with ruptured peptic ulcer. FIG. 5b shows pulsatile bleeding after controlled injury of the internalized gastric artery. FIG. 5c shows successful control of anticoagulated (activated clotting time >250 seconds), arterial bleeding from the wound of FIG. 5b immediately after application of two patches of 2 cm×2 cm nonwoven dressing matrix formed from superfine chitosan fiber (Formulation 25 with 17.6 g/m$^2$ basis weight). FIG. 5d shows the same application from FIG. 5c at about 30 minutes later still successfully controlling bleeding and demonstrating a high level of injury conformance and maintenance of uniform tissue adhesion. FIG. 5e shows superfine chitosan fiber matrix (Formulation 25 with 17.6 g/m$^2$ basis weight) successfully controlling arterial bleeding similar to that shown in FIG. 5b immediately after dressing application. FIG. 5f shows gastric incision closure in a layer fashion to close the abdominal cavity for the 180 minutes to provide for prolonged residence and hemostasis testing of the superfine chitosan fiber matrix within the stomach (Example 3, part b). FIG. 5g shows central visualization after 180 minutes of application of the superfine chitosan fiber matrix dressing (Formulation 25 with 17.6 g/m$^2$ basis weight) by endoscope (gastroscope) with dressing showing a high level of conformity to the stomach wall, uniformly adhering to the stomach mucosa over the arterial injury with complete bleeding control. FIG. 5h shows the same dressing as FIG. 5g, with stomach opened, and contents externalized. FIG. 5h confirms the gastroscope observations in FIG. 5g. FIG. 5i is the dressing from FIGS. 5g and 5h which has been removed from the injury and turned over to reveal the tissue contacting side of the matrix dressing promoting significant clotting over the anticoagulated injury. FIG. 5j shows a central gastroscope image (for comparison purposes) of a less desirable dressing type formed of chitosan matrix, not from nonwoven superfine fiber, which was tested during the same set of 180 minute upper gastrointestinal injury model swine experiments, but in different swine. FIG. 5k shows the same dressing as FIG. 5j, with stomach opened, and contents externalized. FIG. 5k confirms the gastroscope observations in FIG. 5j.

DETAILED DESCRIPTION

A list of studies and their outcomes conducted to prepare chitosan solutions, characterize solution properties, and test the impact of formulation design on the success (or failure) to form superfine fibers by centrifugal spinning is provided in FIGS. 1 and 2. Spinning tests were performed using FiberRio labscale L-1000 Cyclone or pilot scale FE1.1 centrifugal spinning machines.

An index of materials used in the studies with abbreviations and specifications is provided below:

| Material | Vendor | Specification |
| --- | --- | --- |
| AA | Sigma-Aldrich | Glacial Acetic Acid, 99% purity |
| PEO-1 | Sigma-Aldrich | Polyethyleneoxide, Mw = 400 kDa |
| PEO-2 | Sigma-Aldrich | Polyethyleneoxide, Mw = 900 kDa |
| PVA | Fortischem | 15% polyvinyl alcohol aqueous solution, Viscosity: 9-13 mPa · s 4% aq. Solution |
| PVP | BASF | poly-vinyl pyrrolidone (Kollidon 90F) |
| H2O | Facility | Deionized Water |
| Citric Acid | Sigma-Aldrich | Citric Acid, 95% purity |
| Lactic Acid | Sigma | 85-95% purity |
| Chitosan-1 | AK Biotech | 87% DDA, Viscosity: 9 mPa · s, 0.5% aq. Solution, 0.5% AA (25° C.) |
| Chitosan-2 | Primex | 95% DDA, Viscosity: 9 mPa · s 1% aq. Solution with 1% AA (25° C.) |
| Chitosan-3 | Primex | 95% DDA, Viscosity: 45 mPa · s 1% aq. Solution with 1% AA (25° C.) |
| Chitosan-4 | Primex | 92% DDA, Viscosity: 99 mPa · s 1% aq. Solution with 1% A (25° C.) |
| Chitosan-5 | Primex | 85% DDA, Viscosity: 146 mPa · s 1% aq. Solution with % AA (25° C.) |
| Chitosan-6 | Primex | 80% DDA, Viscosity: 390 mPa · s 1% aq. Solution with 1% A (25° C.) |

Formulation parameters included chitosan DDA, Mw (indicated by solution viscosity of 1% aqueous samples of each chitosan), wt % or dry matter content of each formulation, the order of additions of solvents, use or not of ultrasonification and centrifugation to homogenize solutions, concentration of acetic acid, formulation viscosity, presence or absence of polymeric additive and presence or absence of crosslinker. Unless otherwise noted, Formulations 1 to 30 were prepared according to compositions listed in FIG. 1. Solutions were all prepared and stored at room temperature at about 21° C. to 28° C. Reagents used in the solutions preparation were also at room temperature (about 21° C. to 28° C.). Depending on listed order of additions (Formulations 7 to 30), acetic acid was first placed in a glass beaker and chitosan was added and mixed using glass rod. Water was added and mixed manually (using glass or stainless steel rod in case of large volume solution). In Formulations 1 to 7, water was mixed first to disperse the chitosan with acetic acid being added after. The addition of acetic acid first was found to provide for improved homogeneity and ease of mixing of the solutions. The rheological modification agent was mixed separately in water to provide a separate solution which was allowed to sit for 3 days in the case of Formulations 3 to 28 and about 1 day in the case of Formulations 1, 2, 29 and 30. Other than for Formulations 1, 2, 29, and 30 (in which solution mixtures of chitosan/acetic acid/water and rheological modifier/water (if used) were left for 1 day before mixing within about 30 to 120 minutes prior to mixing into the final spinning solution), mixtures were left standing at room temperature (21° C. to 28° C.) for 3 days before mixing into their final spinning solution which was allowed to stand at room temperature (21° C. to 28° C.) for about 3 hours, about 5 hours, for about 8 hours, and about 12 hours before use in a spinning test. In the case of rheological modifier solutions, 3% w/w (aq.), 3.5% w/w (aq.) or 3.75% w/w (aq.) solution was prepared using magnetic stirrer. The mixture was left standing for 1 day (Formulations 29 and 30) or 3 days (Formulations 5, 6, 7, 10 to 18, 20 to 28) at room temperature (21° C. to 28° C.) to equilibrate and homogenize by diffusion processes. After the equilibration time, the chitosan solution was blended together with the rheological modifier solution (for formulations comprising rheological modifier) and mixed manually using glass or stainless steel rods. Centrifugation was used to remove bubbles if present and ultrasonification was applied for about 5 minutes in Formulations 1 to 24 to aid in homogenation of the chitosan/acetic acid/water solutions. Final spinning mixtures were divided into 2 individual aliquots: one for measuring viscosity and the other for fiber spinning tests.

Solutions were characterized at about room temperature (21° C. to 28° C.) for viscosity using a Brookfield viscometer (LVDVII-Pro), spindle LV3.

Evaluation of formulation composition, equilibration and aging on the processability of each liquid formulation into dry, superfine fibers was performed initially on the small-scale laboratory machine (FibeRio, L-1000M Cyclone). Fiber formation tests using this equipment and the resulting fiber materials are presented (See FIGS. 1 and 2 Formulations 1 to 24). Successfully spun superfine fiber samples were separated from the fiber collector for determination of dryness, mass, and characterization by scanning electron microscopy.

A pilot scale centrifugal spinning machine (Fiberio FE1.1) was used to scale formulations that had previously demonstrated successful spinning on the laboratory scale L-1000 machine (See FIGS. 1 and 2, Formulations 25 to 30). The superfine fibers spun from the FE1.1 machine were deposited onto 50 cm wide spunbound substrate web to enable nonwoven fiber collection. The collection distance between the FE1.1 spinnerets head and the spunbound web was between about 7.5 to 25 cm. The spunbound collector webbing was supported on a conveyor system with feed rate at between 10 cm/min and 25 cm/min. Successfully spun superfine fiber samples were separated from the substrate backing (web) for determination of dryness, mass, and characterization by scanning electron microscopy.

Continuous, compliant, chitosan-based superfine fibers and matrices comprising such fibers, and the ability to prepare such fibers and matrices using chitosan solution formulations suitable for centrifugal spinning are highly desirable. Matrices of the present invention also contain varying levels of salt content which can be customized to suit various applications for the spun superfine fiber compositions. Superfine fibers of the present invention have a fiber diameter preferably including microfibers with diameter less than or equal to about 10 microns, about 9 microns, about 8 microns, about 7 microns, about 6 microns, about 5 microns, about 4 microns, about 3 microns, and micron and submicron fibers that are about 2 microns and less, more preferably includes microfibers with diameter less than or equal to about 5 microns and micron and submicron fibers that are about 1 microns and less; and most preferably includes microfibers with diameter less than or equal to about 3 microns and micron and submicron fibers that are about 1 microns and less.

Matrices of the present invention may also include various combinations of superfine fibers having various sizes and mixed in varying ratios.

Superfine fibers such as those of the present invention that relate to bioactive polymer materials such as chitosan are especially beneficial, since such materials formed of superfine fiber not only enhance wound surface conformability, but also enhance overall bioactivity when presented in a matrix dressing. The bioactivity of materials presented in a biological environment is fundamentally associated with bioactive surface functionality of the materials and its specific surface area (defined as the specific surface area being equal to the surface area per unit mass of material). Since specific surface area of a fiber matrix is inversely proportional to fiber diameter, bioactivity will proportionally increase with reduction in fiber diameter.

Another advantage of spinning of polymer solution derived superfine fibers is that the very high surface area of the resultant spun thread allows for rapid solvent removal (drying) and preservation of the functional chemical activity of the original fiber solution composition. Another advantage of spinning superfine fibers with high specific surface area is that their rapid drying allows immediate collection and formation of a clean, homogeneous, nonwoven matrix for biomedical use without need for a secondary step of matrix preparation by a conventional nonwoven or woven processes. Thus, there are significant advantages in the commercial preparation and use of wound dressing and matrix articles comprising bioactive materials with superfine fiber diameters and prepared using the present invention's advanced superfine fiber formation technique that preserves original fiber solution chemical functionality and provides for superfine fiber diameters preferably including microfibers with diameter less than or equal to about 10 microns and micron and submicron fibers that are about 2 microns and less. Superfine fibers of the present invention have fiber diameter with a diameter less than or equal to about 10 microns, about 9 microns, about 8 microns, about 7 microns, about 6 microns, about 5 microns, about 4 microns, about 3 microns, and micron and submicron fibers that are about 2 microns and less, more preferably includes microfibers with diameter less than or equal to about 5 microns and micron and submicron fibers that are about 1 microns and less; and most preferably includes microfibers with diameter less than or equal to about 3 microns and micron and submicron fibers that are about 1 microns and less. Matrices of the present invention may also include various combinations of superfine fibers and/or alteration of spinning processes to produce compositions comprising superfine chitosan-based fibers having various sizes and mixed in varying ratios. It is noted that centrifugal spinning may provide a broad range of fiber sizes. It can also be tailored to provide narrow size distribution of fiber diameter selected by, for example, spinning rpm, distance to collector, solution viscosity, solution concentration, spinning temperature and drying conditions.

The processable fiber diameter range from the centrifugal spinning includes micron to submicron diameter of the bioactive chitosan superfine fiber that is advantageous for realizing high spinning rates of bioactive fiber as well as for allowing promotion of highly desirable pore sizes in the collected nonwoven fiber matrix. Spinning rate through a spinneret is proportional to cross-sectional area of the spun fiber. Pore size in spun fiber matrices is proportional to mean fiber diameter and range of fiber diameter. Too small a fiber diameter such as mean fiber diameter less than or equal to 500 nm in a nonwoven matrix results in mean matrix pore size less than or equal to 1.5 microns which is not conducive to pores which allow for cell infiltration. Typical diameter of red blood cells, platelets, neutrophils, lymphocytes, fibroblasts and chondrocytes are about 8, 3, 10, 15, 12 and 20 microns respectively with preferred interconnected optimal pore sizes of 5 to 40 microns, and even more preferred interconnected pore sizes of 8 to 15 microns, to accommodate the different cell size within a matrix. Pore sizes may range anywhere from, for example, 1 to 6 microns, 3 to 6 microns, 4 to 8 microns, 5 to 8 microns, 5 to 10 microns, 5 to 15 microns, 10 to 15 microns, 10 to 20 microns, 15 to 20 microns, 20 to 30 microns, 25 to 35 microns, and 32 to 40 microns. Spinning allows for a selection of mean fiber size of about 1 to 5 microns which will advantageously provide interconnected mean pore size near 8 to 15 microns for efficient accommodation of different cells and optimal matrix surface contact with the cells.

This invention disclosure provides, for the first time, the ability to spin bioactive superfine chitosan fiber into an inert fluid and quickly collect high basis weight (e.g., greater than about 1 $g/m^2$ relative to conventional electrospun chitosan-based superfine fiber products, or more preferably greater than about 2.5 $g/m^2$, and were still more preferably greater than about 5 $g/m^2$, about 10 $g/m^2$, about 15 $g/m^2$, about 17 $g/m^2$, about 20 $g/m^2$, about 25 $g/m^2$, about 30 $g/m^2$, about 35 $g/m^2$, about 40 $g/m^2$, about 45 $g/m^2$, or greater than or equal to about 50 $g/m^2$) of chitosan-based superfine fiber matrices composed substantially of bioactive chitosan acid salt, or at least composed of at or about 20% w/w chitosan, about 25% w/w chitosan, about 30% w/w chitosan, about 35% w/w chitosan, about 40% w/w chitosan, about 45% w/w chitosan, about 50% w/w chitosan, about 55% w/w chitosan, about 60% w/w chitosan, about 65% w/w chitosan, about 70% w/w chitosan, about 75% w/w chitosan, about 80% w/w chitosan, about 85% w/w chitosan, about 90% w/w chitosan, about 95% w/w chitosan, or about 100% w/w using centrifugal spinning that is capable of production rates greater than about 1 g/min of bioactive superfine fiber production from one or more spinnerets with stable spinning rates and without process interruptions associated with basis weight of fiber matrix collected.

Percentages of w/w chitosan noted in the specification include any contribution by weight of associated salt, if any. There are ways to determine what percentage by weight of the chitosan-based fiber is due to the presence of a salt. For example, the glucosammonium acetate salt w/w percentage in dried chitosan-based fibers from aqueous chitosan acetate solution is dependent on percentage degree of deacetylation and drying environment. That is, in dried (drying atmosphere of air or inert gas such as nitrogen or argon with temperature, for example, at or less than 85° C. and with humidity at or less than 40%) glucosammonium monomer in chitosan of 80% degree of deacetylation with only bound acetic acid salt and there will be no free acetic acid, such that the percentage acetic acid that is bound may be determined to be about 14% to 18% by weight. For comparison, typically in dried (drying atmosphere of air or inert gas such as nitrogen or argon with temperature, for example, at or less than 85° C. and humidity at or less than 40%) glucosammonium monomer in chitosan of 40% degree of deacetylation with only bound acetic acid salt and no free acetic acid, the percentage acetic acid that is bound is about 7% to 9% by weight. For comparison, typically in dried (drying atmosphere of air or inert gas such as nitrogen or argon with temperature, for example, at or less than 85° C. and humidity at or less than 25%) glucosammonium monomer in chitosan of 25% degree of deacetylation with only bound acetic acid salt and no free acetic acid, the percentage acetic acid that is bound is about 2% to 5% by weight. For comparison, typically in dried (drying atmosphere of air or inert gas such as nitrogen or argon with temperature at about 125° C. and humidity at or less than 40%) glucosammonium monomer in chitosan of 80% degree of deacetylation with only bound acetic acid salt and no free acetic acid, the percentage acetic acid that is bound is about 2% to 5% by weight.

The superfine chitosan-based fibers of the present invention also may be characterized by beneficial adhesive qualities or properties imparted by salt residues left with the superfine chitosan fibers. Exemplary chitosan acid salts for preparation of superfine chitosan-based fibers in accordance with the present invention include, but are not limited to, chitosan acetate salt, chitosan lactic acid salt, chitosan citric acid salt, chitosan glycolic acid salt, chitosan chloride acid salt, chitosan succinic acid salt, chitosan glutamic acid salt, or combinations of these chitosan acid salts in the same chitosan fiber. These chitosan acid salts provide for the bioactive mucoadhesion property of tissue wetting and tissue adhesion. If tested for tissue adhesion properties, these chitosan acid salt fibers and their nonwoven matrices will demonstrate uniaxial orthogonal tensile resistance to removal from contact with tissue (adherence) determined by a uniaxial mechanical testing machine which ranges from greater than about 1 kPa to about 200 kPa. The chitosan acid salt tissue adherence strength is dependent on clean contact of the chitosan with wet or wetted (blood or biological fluid such as, for example, saliva) tissue, type of chitosan acid salt, fraction of salt in the chitosan at time of contact (and at time of testing), and cohesion strength of the wetted fiber or fiber matrix.

This invention disclosure includes, for example:

1. Chitosan-based solution formulations for preparation of dry centrifugally spun chitosan-based superfine fibers less than about 10 microns mean diameter with a chitosan content in the fiber preferably greater than about 20% w/w, more preferably greater than about 50% w/w, and most preferably greater than about 80% w/w, and wherein the original spinning solution formulation chitosan acid salt chemical functionality is preserved in the superfine spun fiber and in any products comprising the superfine spun fiber.

2. Centrifugal spinning methods for preparation of dry chitosan-based superfine fiber less than about 10 micron mean diameter with chitosan content in the fiber preferably greater than about 20% w/w, more preferably greater than about 50% w/w, and most preferably greater than about 80% w/w, comprising one or more of spinning continuously, spinning at greater than about 1 g/min, producing a spun superfine fiber product with basis weight greater than about 2.5 g/m$^2$, more preferably greater than about 15 g/m$^2$, and most preferably greater than about 30 g/m$^2$, and preserving the original spinning solution formulation chitosan acid salt chemical functionality in the superfine fiber and, optionally, in any products comprising the superfine spun fiber.

3. Formulations for final high basis weight dry chitosan-based matrices, composed substantially of bioactive chitosan acid salt superfine fibers less than about 10 micron mean diameter with a chitosan content in the fiber preferably greater than about 20% w/w, more preferably greater than about 50% w/w, and most preferably greater than about 80% w/w, with basis weight greater than about 2.5 g/m$^2$, more preferably greater than about 15 g/m$^2$, and most preferably greater than about 30 g/m$^2$, and, wherein the matrices are, optionally, spun continuously from centrifugal spinning techniques, and able to be spun at greater than about 1 g/min from one or more spinnerets with stable spinning rates and without process interruptions associated with basis weight of fiber matrix collected. Matrices of the present invention provide for high specific surface area, cell compatible pore diameters in the range of 1 to 20 microns which are highly desirable for wound care, drug delivery, regenerative medicine, and tissue engineering applications.

4. The present invention superfine fibers, superfine fiber product, fiber formulations, and centrifugal spinning methods provide for high basis weight bioactive chitosan acid salt superfine fiber materials and matrices with high specific surface area, cell compatible pore diameters in the range of 1 to 20 microns which are highly desirable in wound care management and particularly in controlling bleeding; and bleeding in difficult to access wounds such as those needed to be accessed in minimally invasive surgical applications including but not limited to laparoscopy, gastroscopy, endoscopy and arthroscopy.

5. Methods for treating wounds, bleeding, or otherwise encouraging hemostasis or healing by using or application of the materials and methods of the present invention are also contemplated.

Bioactive chitosan acid solution formulations for preparation of centrifugally spun chitosan-based superfine fiber less than about 10 micron mean diameter with chitosan composition in the fiber preferably greater than about 20% w/w were first screened for ability to centrifugally spin using a laboratory scale Forcespinning® L-1000M Cyclone machine (FibeRio® Technology Corporation) with a "cotton candy" collector. In the case of centrifugal spinning from the laboratory L-1000 machine, the solution reservoirs are provided by two, equally weighted, initially charged (volumes of about 1.0 to 1.5 ml solution each), equally loaded, horizontally opposed cylinders (internal diameter of about 0.7 to 1.5 cm each) capped with open end hypodermic needles (about 12 to 34 gauge or 2.16 to 0.08 mm internal diameter each) pointing outwards, all attached to a centrifugal rotor capable of controlled spinning rate with spinning up to about 20,000 rpm. The "cotton candy" collector is formed of equally spaced vertical upright columns each between 20 cm to 50 cm long arrayed circumferentially around the L-1000 spinnerets and with distance between the columns and spinnerets (hypodermic needles) such that any fiber stream spun centrifugally from the spinnerets is caught by the array. Typically the distance from the spinnerets to the upright collector columns may be from between about 5 to 50 cm. The collection system may be accessed during spinning to collect the spun nonwoven material for determination of dry matter content and basis weight (g/m$^2$). The collected samples may be sent for scanning electron microscope determination of nonwoven matrix structure, presence of particles, fiber diameter distribution, and pore size distribution.

The chitosan spinning solution formulation compositions of the invention contained chitosan with or without a water soluble, rheological modifier, with or without a crosslinker, an acid and water. Chitosan is defined herein as the linear polymer of poly-β-(1-4)N-acetyl D-glucosamine composed of at least ten (10) linked monomer units that may include D-glucosamine and N-acetyl D-glucosamine monomers with β-(1-4) glycosidic linkages and that is soluble in dilute aqueous acid solution. Water soluble rheological modifiers are water soluble molecules including, but not limited to, urea, polyethylene oxide, polyvinyl alcohol, and polyvinylpyrolidone that when present in solution enable modification of intermolecular solution forces thus providing for improved intermolecular alignment and reduction of polymer solution shear strain under an applied solution shear stress and thus can provide for conditions more conducive to successful chitosan superfine fiber spinning. Viscous behavior in a fluid is characterized by viscosity measurement and results from shear strain changes occurring in a fluid caused by application of shear stress. Rheological modifiers often also demonstrate surface active modification of fluid properties. In the case of polyethylene oxide polymers, reduction of fluid surface tension in spinning fluids or solutions provides added benefit to their rheological modification characteristics.

The chitosan content in the spinning solution formulation was targeted and tested as high as 10% w/w with a rheological modifier in the solution formulation as low as 0.0% but in an amount sufficient to provide for efficient superfine spinning. Inclusion of a crosslinker in the spinning solution that can be activated after spinning may be desirable in dry matrices to provide for enhanced matrix resistance to degradation or dissolution. Crosslinking agents may include, but are not limited to, a multifunctional organic acid such as citric acid, 1-Ethyl-3-[3-dimethylaminopropyl]carbodiimide hydrochloride (EDC), collagen and gelatin. Acids may include, but are not limited to, acetic acid, hydrochloric acid, glycolic acid, glutamic acid, citric acid, succinic acid, carbonic acid, ascorbic acid, and lactic acid.

Initial screening of centrifugal spinning ability to spin chitosan solution formulations into chitosan superfine fiber was performed using the Forcespinning L-1000 machine (Formulations 1-23). Similar to Xu et al. 2014a; Xu et al. 2014b, it was found that chitosan aqueous solutions from low percentage of chitosan solution formulations (2% w/w) to a higher percentage of chitosan solution formulations (7% w/w) with an elevated percentage (≥20% w/w) of polymeric material being chitosan were not able to spin using centrifugal spinning (Formulations 1-9). These initial studies (Formulations 1-9) were performed without a rheological modifier. It was found that the presence of a rheological modifier between 5% to 10% w/w in the final dried fiber was desirable for successful centrifugal spinning of the chitosan fibers. The final spun fibers and their nonwoven matrices were heat treated between 80° C. to 160° C. for between about 10 minutes to 48 hours to stabilize the fiber against collapse and dissolution when contacting water, wound exudate, and other biological fluids such as blood. More preferably, heat treatment ranges from between about 10 minutes to about 30 minutes, with heating at about 110° C. to about 135° C., and with most preferred treatment being about 20 to about 30 minutes at about 115° C. to about 130° C. In absence of this heat treatment, the fibers instantly dissolved and matrices instantly collapsed in the presence of water, wound exudate, and other biological fluids such as blood. The heat treatment provided for reduction in the % fraction of the acetic acid salt and also provided for annealing of the paracyrstalline structure of remaining polymeric chitosan acid salt into a more dissolution resistant matrix structure. The heat treatment of the present invention may beneficially be modified to adjust the final salt content of the resulting fibers. Accordingly the bioactivity and adhesiveness of the superfine fibers and/or the compositions comprising the superfine fibers may be controlled or fine-tuned to meet the needs of different applications.

Targeting and testing higher percentage chitosan solution formulations and using a Brookfield viscometer (LVDVII-Pro) with LV3 spindle at 25° C., viscosity of the formulation solutions was found to increase with increasing % acetic acid until a critical point at high percentage of acetic acid, at which point there was a sudden and unanticipated drop in viscosity of the chitosan solution to a significantly lower value. High percentage weight fraction of acetic acid near to above 70% acetic acid was targeted and tested in the formulations in order to provide for more rapid evaporation of the solvent in order to preserve the fibers in collection. This is because it was found that wet fibers immediately collapse to form macroscopic films if deposited on the collector. It was found that a small reduction in percentage acetic acid content in the formulations closer to about 60% w/w provided for centrifugal spinning of the formulations.

Investigation of a range of chitosans of different degrees of deacetylation and different 1% chitosan solution viscosity properties (low to high viscosity) within the percentage chitosan formulation weight fraction of about 2 to 7% w/w and acetic acid percent weight fraction of about 50 to 60% w/w resulted in successful centrifugal spinning of some chitosan solutions when screening on the L-1000 benchtop machine (Formulations 10 to 24). Although it was found that inclusion of polyethylene oxide (PEO) was generally necessary at around 5 to 10% w/w in the final dry fiber matrix for successful fiber spinning, it is contemplated that conditions involving a high chitosan percentage fraction at or approaching 100% chitosan as the polymer component in the final dried matrix are possible using only slightly different solution spinning conditions and formulation composition.

Centrifugal spinning scale-up testing was performed on a pilot scale FE1.1 FiberRio centrifugal spinning machine through which polymer fluid solution can be pumped at maximum feed rate of about 20 g/minute through a central feed line to the centrifugal spinning head containing spinnerets on the spinning head. The spinning head diameter of the FE1.1 may be about 7.5 cm, about 12.5 cm, about 20 cm, and about 25 cm. The spinneret openings may extend radially to about 0.0 cm, about 1.0 cm, about 2.0 cm and about 3.0 cm from the outer surface diameter of the spinning head. The spinneret orifice internal cross-sectional area is about 3.7 mm$^2$ to about 8×10$^{-5}$ mm$^2$ (equivalent to internal diameters of about 2.16 mm to about 0.01 mm). The FE1.1 rotation speed of the spinning head is controllable to a set revolutions per minute (rpm) up to a maximum rotation speed of 25,000 rpm. The spun fiber from this machine is collected circumferentially onto a conveyor train with about a 50 cm or about a 100 cm wide collector oriented perpendicular to the fiber flow and able to support a collector sheet composed of open mesh, non-adhesive, polypropylene spunbound mat of basis weight at about 25 to 250 g/m$^2$. The conveyor rate collector train, depending on setting, feeds at between 2.5 to 50 cm per minute. The radial distance between conveyor train and the spinnerets is adjustable between about 5 cm to 50 cm. An inert collector fluid, which is typically air at controlled temperature and humidity, is applied against the newly formed fiber streaming from the spinnerets to cause them to solidify and be collected against the spunbound mat on the collector train. After passing over the collector train, the collector fluid is exhausted to the external environment. The collection system may be accessed during spinning to collect the spun nonwoven material for determination of dry matter content and basis weight (g/m$^2$). The collected samples may be sent for scanning electron microscope direct determination of nonwoven matrix structure, presence of particles, fiber diameter distribution and pore size distribution. Small volume formulations that demonstrated the ability to spin on the Forcespinning laboratory scale L-1000M subsequently were able to be spun as higher volume formulations on the scale-up pilot FE1.1 machine (see Formulations 25 to 30).

Example 1 details results from the pilot scale experiments. The fiber sample with basis weight 17.6 g/cm$^2$ from Formulation 25 was subsequently evaluated a) for tissue adhesion and stability (see example 2) and b) hemostatic efficacy in an anticoagulated swine injury model of gastrointestinal bleeding (see example 3).

Example 1. Formulations 25-30, Example Fiber Tests: Spinning on Production Scale Forcespinning® FE 1.1 (FibeRio Technology Corporation)

Tables 1, 2 and 3 demonstrate the spinnability under centrifugal spinning in a pilot scale machine (FE1.1) of chitosan-based solutions with polymer content of 89% w/w chitosan and 11% w/w polyethylene oxide (400 kDa). The one polyvinylodine pyrolidone (PVP) formulation (#30) did not successfully spin. Typical flow rate of the chitosan solutions from the FE1.1 during spinning was about 5.0 g/min with fastest flow rate being about 8.0 g/min from the spinning head. As the highest expected flow rate specified for the FE1.1 is 20 g/minute of solution, the test solution of spinning of the chitosan at 5.0 g/min (about 25% of maximum) and 8 g/min (about 40% or maximum) indicates that chitosan solutions may be efficiently processed using centrifugal spinning methods.

TABLE 1

Formulation Compositions

| Formula | Polymer (% w/w) | Chitosan | Chitosan (g) | Water (g) | Acetic acid (g) | Rheol solution (g) |
|---|---|---|---|---|---|---|
| 25 | 7.5 | Chitosan-2 | 80.4 | 638.9 | 155.8 | 327.4¶ |
| 26 | 7.5 | Chitosan-2 | 73.5 | 142.4 | 584.1 | 300.0¶ |
| 27 | 5.5 | Chitosan-2 | 58.9 | 250.4 | 650.0 | 240.3¶ |
| 28 | 7.5 | Chitosan-2 | 59.8 | 115.9 | 475.5 | 244.1¶ |
| 29 | 7.5 | Chitosan-2 | 175.3 | 339.5 | 1392.2 | 716.7¶ |
| 30 | 8.0 | Chitosan-2 | 17.7 | 34.2 | 140.2 | 58.7† |

¶weight of 3.0% w/w PEO-1 (aq.)
†weight of 3.75% w/w PVP (aq.)

TABLE 2

Viscosities (LV3 spindle) and dry matter content of chitosan solutions

| Formula | Temp. | RPM | Torque | Viscosity | Chitosan | PEO | Dry matter cont. Theor. | Measured |
|---|---|---|---|---|---|---|---|---|
| 25 | 22.8 | 1 | 100 | 120 | 6.7 | 0.7 | 7.5 | — |
| 26 | 27.7 | 1.68 | 97 | 69.5 | 6.7 | 0.7 | 7.5 | 8.2 |
| 27 | 27.1 | 64 | 99 | 1.86 | 4.9 | 0.6 | 5.5 | 6.1 |
| 28 | 28.6 | 3.7 | 99 | 32 | 6.7 | 0.7 | 7.5 | 7.9 |
| 29 | 22 | 2.7 | 97 | 44.0 | 6.7 | 0.8 | 7.5 | — |
| 30 | 22 | 2.9 | 97 | 40.2 | 7.1 | 0.9 | 8.0 | — |

The porosity and fiber diameter range of the spun chitosan solutions (Table 3) determined by direct inspection of the nonwoven spun matrices are optimal or very close to optimal for bioactive chitosan superfine fiber matrix use in wound care, regenerative, and medicine minimally invasive surgery applications. The basis weights of the matrices is within the acceptable range for these wound care applications and may be increased by improved efficiency in the spinning flow rate through the FE1.1 spinnerets on the spinning head and also by layering with application of more than one spinning head.

Example 2. In Vitro Testing of Superfine Chitosan Fiber for Tissue Adherence, Foldability and Resistance to Dissolution in a Harsh Biological Environment Such as the Stomach Introduction: Tissue adherence, foldability and resistance to dissolution in harsh biological environments such as the stomach are highly desirable characteristics of superfine chitosan fiber nonwoven matrices intended for medical applications including external wound care, internal implantation, drug delivery, hemostasis application, and delivery by endoscope or catheter for minimally invasive wound care and hemostasis.

a) Dissolution resistance against synthetic gastric fluid at 37° C. was investigated as follows. Synthetic gastric fluid was prepared according to formulation of Pepsin (1.6 g), NaCl (1 g), water (500 ml) with all added to a Nalgene LDPE 1000 ml bottle and mixed. The acidity was adjusted to be between pH 3 to 4 using Millipore pH 0-14 universal indicator strips and dropwise addition of 3.0 M HCl. Dropwise addition of 1.0 M NaOH was used to raise the pH if required. The gastric fluid testing was performed in a beaker test method.

Briefly, in the beaker method the following was performed. A 38 mm×38 mm piece of fresh stomach mucosa was adhered inside a polystyrene beaker (250 ml, Fisher Catalog No. 08-732-124) at its base using a thin layer of cyanoacrylate adhesive applied using a cotton swab. The mucosa surface prior to gluing was dabbed dry using Texwipe tissue. The adhesive was allowed to dry over 2-5 minutes. After becoming fully adhered to the beaker, the top exposed tissue surface was wetted drop-wise (generally 2 drops) with citrated whole bovine blood, and a 20 mm×20 mm piece from a test article sheet was adhered to the blood covered mucosa surface by application of 500 g of load applied orthogonally to the mucosa surface for 1 minute through a 25 mm diameter PVC flat head probe. Synthetic

TABLE 3

Fiber tests using pilot FE1.1: fiber spinning conditions and results

| Fiber Test Formula | Temp (° C.) | RH % | RPM | Spinner height | Web Speed (cm/min) | SPUN | Layers | Basis wt. (g/m²) | Fiber diam. (nm) | Pore diam. (microns) |
|---|---|---|---|---|---|---|---|---|---|---|
| 25 | 25 | 48 | 8000 | 8 | 10 | Y | 4 | 17.6 | 100-400 | 1-7 |
| 26 | 34-37 | 33-40 | 8000 | 8 | 10 | Y | 1 | 3.6 | 100-2000 | 1-8 |
| 27 | 34-37 | 33-40 | 8000 | 8 | 25 | Y | 1 | 2.0 | 100-2000 | 1-4 |
| 28 | 34-37 | 33-40 | 7000 | 8 | 10 | Y | 1 | 3.43 | 200-3000 | 2-8 |
| 29 | 34-37 | 47 | 10000 | 13 | 20 | Y | 1 | 4.0 | 100-1000 | 1-3 | gastric fluid at room (about 90 ml) was added to the beaker. Parafilm was used to seal the beaker and the beaker is placed upright on an IKA KS260 orbital shaker in an incubator at 37° C. under mild shaking (130 rpm). The inside of the beaker was monitored hourly until demonstrable separation from mucosa and/or dissolution/fragmentation of the sample was observed and the time to separation/dissolution/fragmentation was recorded. The control in this test were freeze dried chitosan acetate sponge matrices formed to densities near 0.25 g/cm$^3$. The superfine chitosan fiber test article was Formulation 25 from FIG. 2 with basis weight 17.6 g/m$^2$ and applied in a single layer.

Results of the testing showed that chitosan freeze dried dressing controls, though initially adherent to the stomach mucosa and water resistant, lasted less than 15 minutes intact in the synthetic gastric fluid at 37° C. Typically the freeze dried chitosan control dressings showed signs of fragmentation and detachment from the mucosa site at about 10 to 15 minutes of exposure to the synthetic gastric fluid. Most surprisingly, the superfine chitosan fiber nonwoven material, though of considerably lower density than the control, more porous than the control and with fiber diameter close to submicron was able to resist dissolution, detachment and degradation for at least 120 minutes of exposure to the severe test environment.

This novel behavior of the superfine chitosan fiber was highly unexpected given the general enhanced susceptibility of high specific surface area enzyme sensitive materials to enzymatic degradation. Since chitosan is well known to be susceptible to rapid dissolution and degradation in a pepsin acid environment it is hypothesized that the particular orientation process of the superfine fiber production combined with the brief 125° C. heat treatment imparted enhanced resistance to the pepsin acid combination of the stomach.

b) The superfine chitosan fiber nonwoven matrices were tested for their ability to mechanically fold without tearing or cracking. Briefly, Sample sheets were folded 180° along length and width axes and the crease line was compressed. Dry test sheets (25 mm×25 mm) were unfolded and indications of tearing or cracking were recorded.

Results of testing were that the superfine chitosan nonwoven matrices demonstrated excellent and superior folding and unfolding capabilities compared to chitosan control materials which were not formed of chitosan superfine nonwoven matrices.

c) The superfine chitosan fiber nonwoven matrices were tested for tissue adherence. Briefly, a uniaxial mechanical tester (Instron 5844) with 10 N load cell was used to investigate wet adhesion to swine mucosal tissue (from swine stomach). Adhesion testing was performed using ASTM F2258-03 "Standard Test Method for Strength: Properties of Tissue Adhesives in Tension." Testing was performed with a testing configuration with lower and upper PVC probes uni-axially aligned in the z vertical direction so that the edges of their x-y horizontal, 15.2 mm diameter faces would accurately (±0.2 mm) coincide with each other with uniaxial lowering of the top probe which was supported on the upper, movable Instron crosshead in chuck fixture. The lower PVC probe was supported in a stationary, bottom, chuck fixture. The bottom PVC horizontal surface was used to support a 10 mm×10 mm swine mucosal tissue sample adhered at least 5 minutes before testing by cyanoacrylate glue to the PVC surface. The top PVC horizontal surface was used to support a 10 mm×10 mm chitosan superfine fiber test piece that was adhered by a 3M double side tape at least 5 minutes before testing. The square tissue piece was wetted with 0.25 ml of citrated bovine whole blood prior to lowering the probe onto the test surface. The probe was lowered at 10 mm/min until a maximum load of 0.98 N was reached. At contact, the test and tissue pieces contacted accurately (±0.2 mm) and were mutually co-planar. The uniaxial probe load at 0.98 N was maintained for 30 seconds after which the probe was removed at 10 mm/min and maximum failure stress was recorded.

Results of testing of superfine chitosan nonwoven matrix (FIG. 2, Formulation 25) applied as a 6-layer mat were adherence of: 0.86, 1.47, 2.13, 1.82, and 0.92 kPa (N=5). The average adherence was 1.44 kPa with standard deviation 0.55 kPa.

Example 3. Swine Injury Model of Hemostasis with Evaluation of Chitosan-Based Superfine Nonwoven Fiber Efficacy with Manual Application in a Stomach Injury: a) 15 Minutes after Application; and b) with Closure and Evaluation of Hemostasis at 180 Minutes Inside Stomach by Gastroscopic Evaluation Introduction:

The application observations and successful bleeding control of arterial bleeding in the anticoagulated bleeding models described in this example demonstrate not only broad applicability of the tissue adherent superfine chitosan fiber of the invention to addressing wound care, bleeding, and fluid loss in general wound care, but it also demonstrates specific suitability for addressing wound care, bleeding, and fluid loss in minimally invasive procedures such as control of upper gastrointestinal bleeding.

Methods:

All experiments were performed in accordance with the 2011 National Research Council, "Guide for the Care and Use of Laboratory Animal" and applicable federal regulations. The protocol for the animal study strictly adhered to the NIH Guidelines for the Care and Use of Laboratory Animals and is approved by the Institutional Animal Care and Use Committee.

After anaesthetizing the swine, the surgical site was shaved and scrubbed with chlorhexidine rinse solution and draped in a sterile fashion. A midline laparotomy was performed to expose the stomach. A 5 cm segment of the gastroepiploic vessels were dissected free from the gastric wall. A 1 cm gastronomy was made adjacent to the free but intact arterial blood vessels. The main artery was then pushed through the gastronomy and positioned so that it was exposed to the gastric lumen. The gastric incision was then closed in a standard manner. An approximate 12 cm incision was made on the anterior gastric wall to expose gastric cavity. The inside of the stomach was then externalized to expose the main artery which had been placed inside the gastric cavity (FIG. 5a).

Intravenous heparin was administered intravenously to anticoagulate the animal and achieve a target elevated activated clotting time near 250 seconds.

A 2 to 3 mm long incision injury was made in the internalized main gastric artery sufficient to achieve pulsatile bleeding (FIG. 5b) with bleeding rate of about 2 to 7 g/minute.

To test hemostasis for 180 minutes with closure of test application inside swine stomach the following steps were performed. The gastric incision was closed in a layer fashion. Then the abdominal wall was closed for 3-hours observation. At completion of 3-hours application, an upper endoscopy (GIF Type Q180, Olympus Gastroscope) was performed to identify the wound dressings for a visual examination. Then the incisions of abdomen and stomach were reopened for gross examination of the dressings.

Blood samples for determination of activated clotting time (ACT) level were drawn after 10 minutes and then every 20 minutes during the procedure with additional heparin given IV as needed to maintain the ACT near 250 seconds. ECG, blood pressure, and oxygen saturation were monitored during surgery and recovery. Vitals were recorded every 15 minutes until swine was in recovery and extubated. These parameters included, but were not limited to: blood pressure, % isoflurane, $O_2$ flow, respiratory rate, heart rate, $SpO_2$, capillary refill time, blood pressure with the mean arterial pressure, and body temperature.

a) Injury Testing Against Gauze Control Over 15 Minutes on Externalized Injury Superfine chitosan matrix (Formulation 25) test pieces (2 cm×2 cm) were tested for hemostatic performance on the heparinized swine upper gastrointestinal (UGI) bleeding model against a negative control. Since the basis weight of the dry nonwoven chitosan matrix was about 17 g/m² which is about one third to one quarter of the basis weight of a single layer of the control dressing, overlays (or multiply-plies) of the nonwoven dressing of up to 6 layers for an individual application was allowed in the testing.

Standard surgical gauze (8-ply 2 cm×2 cm) was used as the negative control. Testing of treatment and control was performed by placement of dressing application centrally over the injury with light pressure for a short duration. If bleeding was observed, two additional pressure applications were allowed. If bleeding persisted after the third application, the test was considered a failure. If hemostasis was achieved, the test material was left in place to maintain hemostasis for 15 minutes. A summary of test results is provided in Table 4. Successful control of bleeding is shown during primary application (FIG. 5c) and at around 30 mins (FIG. 5d.).

Results:

Nine out ten samples of superfine chitosan fiber material achieved hemostasis compared to three out of nine negative control dressings (Table 4).

TABLE 4

Assessing Anticoagulated Hemostatic Efficacy of Superfine Fiber vs. Standard Gauze 15 minutes after Application

| Treatment | Animal ID | #Successful | #Failures |
| --- | --- | --- | --- |
| Superfine Chitosan | 1 | 2 | 0 |
|  | 2 | 3 | 1 |
|  | 3 | 4 | 0 |
| Gauze Control | 2 | 1 | 4 |
|  | 3 | 2 | 2 |

Images FIG. 5c and FIG. 5d demonstrate superfine chitosan control of bleeding when first applied (FIG. 5c) and about 30 minutes after application (FIG. 5d).

Additional surgical observations were made and summarized as follows: as well as being highly effective in quickly controlling anti-coagulated (heparinized) bleeding, the superfine fiber chitosan matrix dressing demonstrated highly desirable absence of any significant (about negative and positive 10% change, and more preferably, about negative and positive 5% change) expansion, shrinkage, or distortion in length or width when wetted and present on the injury site. There may have been some small increase in the height of the attached dressing on absorption of blood and other biological fluid but this change was not considered significant to the function of the dressing in an external wound care application, in an internal wound care implant application, or in a minimally invasive procedure such as attachment to the mucosa of the stomach to control of bleeding, or similar control of bleeding or other fluid control in other types of minimally invasive procedures including control of bleeding in transurethral prostatectomy.

The wetted superfine chitosan dressing was found to be highly compliant and readily conformable to the wound surface (FIG. 5d).

A highly desirable characteristic of the superfine chitosan fiber composition of the invention is that it can be applied in layers (FIG. 5c and FIG. 5d) over previous superfine chitosan fiber dressing applications should this be necessary to control difficult to control bleeding, or if the injury size or bleeding area is larger than the size of the superfine chitosan fiber dressing being applied. Clotted blood was observed on the surfaces of the chitosan superfine fiber matrix upon the removal of the test articles indicating a high level of bioactive promotion of clot formation even under conditions of significant anticoagulation. The dressings were uniformly adhered to the mucosal tissue of the stomach (FIG. 5d). They were easily attached to remain in place against an arterial injury for a short duration with application of light hold pressure.

b) Injury Testing Over 180 Minutes Inside Closed Stomach

Superfine chitosan matrix (Formulation 25) test pieces (2 cm×2 cm) were tested for hemostatic performance on the heparinized swine upper gastrointestinal (UGI) bleeding model with closure within the stomach within 5 to 10 minutes after injury with subsequent observation of hemostasis (bleeding control) over 180 minutes. Testing of treatment dressing was performed by placement of dressing application centrally over the injury with light pressure for a short duration. If bleeding was observed, two additional pressure applications were allowed. If bleeding persisted after the third application, the test was considered a failure. If hemostasis was achieved, the application was observed for about ten minutes then the externalized stomach with successful primary hemostasis application (FIG. 5e.) was pushed back into the stomach and the gastric incision was closed in a layer fashion (FIG. 5f) to close the abdominal cavity for the 180 minute application period within a closed stomach. After 180 minutes of application, an upper endoscopy (GIF Type Q180, Olympus Gastroscope) was performed to investigate the injury site and evidence of continued hemostasis by visual examination. Following this investigation, the incisions of abdomen and stomach were reopened for gross examination of the injury site and the dressing application. Images FIG. 5g, FIG. 5h and FIG. 5i demonstrate the successful application of the superfine chitosan fiber nonwoven dressing to control anticoagulated bleeding for 180 minutes inside the closed swine stomach with promotion of clotting at the injury site and maintenance of uniform tissue adherent contact of the dressing over the injury without demonstration of any significant change in dressing size or shape. FIG. 5g is the endoscopy gastroscope image of the dressing. FIG. 5h. is the externalized gross examination of the dressing still attached with uniform tissue adhesion to mucosa of the stomach over the injury site. FIG. 5i is the superfine chitosan fiber dressing removed from the injury site and turned over to demonstrate occurrence of significant blood clots which were formed by the presence of the superfine chitosan fiber nonwoven dressing over the anti-coagulated site of bleeding.

FIG. 5j and FIG. 5k are supplied as examples of dressings which were tested during the same set of experiments but in different swine in the same 180 minute upper gastrointestinal injury model but formed of chitosan matrix not from nonwoven superfine fiber. Given that the dressings in FIG. 5j and FIG. 5k looked very similar on primary application to FIG. 5e, the contrast between the gastroscope dressing images of FIG. 5g and FIG. 5h (both from superfine fiber) and FIGS. 5j and 5k (both not from superfine fiber) are highly instructive. The superfine chitosan fiber dressing in FIG. 5e, FIG. 5g, FIG. 5h, and FIG. 5i. demonstrated (highly desirable) insignificant dressing length, width and height change while adhered to the stomach mucosa over the site of injury for 180 minutes. In contrast, the other dressings of chitosan, but not of superfine fiber, shown in FIG. 5j and FIG. 5k, which surprisingly were able to maintain hemostasis for 180 minutes while adhered only to a single small area over the injury, demonstrated highly undesirable swelling (significant expansion in dressing length width and height), after 180 minutes in the stomach, which distorted the dressings and caused a significant part of the dressings to become detached from the wound and caused the dressings to fold over themselves. Although not fully detached from the wound at 180 minutes, it is anticipated that the swelling, folding and distortion in dressings shown in FIG. 5j and FIG. 5k would eventually have led to their undesirable and premature detachment from the injury site.

The invention claimed is:

1. A bioactive composition comprising:
   at least ten to fifty layers of non-woven chitosan-based fibers having a mean interconnected pore size between 1.5 to about 40 microns, wherein the non-woven chitosan-based fibers in at least one of the layers consist of a combination of:
   (a) centrifugally spun chitosan-based fibers with a diameter less than or equal to about 10 microns and greater than 2 microns; and
   (b) centrifugally spun chitosan-based fibers having a diameter less than or equal to 2 microns,
   wherein the non-woven chitosan-based fibers comprise chitosan consisting of linear polymers of poly-$\beta$-(1-4) N-acetyl D-glucosamine comprising at least ten (10) linked monomer units of D-glucosamine and N-acetyl D-glucosamine monomers with $\beta$-(1-4) glycosidic linkages, wherein the non-woven chitosan-based fibers in the at least one layer have a mean fiber diameter greater than 0.5 microns, and wherein the non-woven chitosan-based fibers in the at least one layer have a chitosan content of at least about 20% (w/w) and an optional chitosan salt.

2. The composition of claim 1, wherein the centrifugally spun chitosan-based fibers with a diameter less than or equal to about 10 microns and greater than 2 microns have a diameter less than or equal to about 5 microns and greater than 2 microns.

3. The composition of claim 1, wherein about 70 to 90% (w/w) of the composition is non-woven chitosan-based fibers.

4. The composition of claim 1, further comprising a chitosan salt.

5. The composition of claim 4, wherein the salt is selected from at least one of chitosan acetate salt, chitosan lactic acid salt, chitosan citric acid salt, chitosan glycolic acid salt, chitosan chloride acid salt, chitosan succinic acid salt, chitosan glutamic acid salt, or combinations of these chitosan acid salts.

6. The composition of claim 4, further comprising fibers having annealed paracrystalline polymeric chitosan acid salt structures.

7. The composition of claim 1, wherein the non-woven chitosan-based fibers are adhesive upon wetting.

8. The composition of claim 1, wherein the non-woven chitosan-based fibers change less than about 10% in length or width upon wetting.

9. The composition of claim 1, wherein the composition has a basis weight of at least 1 g/m$^2$.

10. The composition of claim 1, characterized by a mean interconnected pore size of between about 5 to about 15 microns.

11. The composition of claim 1, further comprising a rheological modifier.

12. The composition of claim 1, wherein about 90 to 100% (w/w) of the composition is non-woven chitosan-based fibers.

13. The composition of claim 1, further comprising non-woven chitosan-based fibers that are heat treated or cross-linked.

14. The composition of claim 1, wherein the non-woven chitosan-based fibers are characterized by a mean interconnected pore size of between about 8 to about 15 microns.

15. The composition of claim 11, wherein the rheological modifier is present in an amount between about 5% and about 10% (w/w).

16. The composition of claim 11, wherein the rheological modifier includes urea, polyethylene oxide, polyvinyl alcohol, or polyvinylpyrrolidone.

17. The composition of claim 1, further comprising non-woven chitosan-based fibers having a diameter of 2 microns.

18. The composition of claim 1, wherein the non-woven chitosan-based fibers have a mean diameter between 0.4 to about 7.0 microns.

19. The composition of claim 18, wherein the mean pore size is about 1 to 25 microns.

20. The composition of claim 1, wherein said composition includes at least 80% void volume.

21. The composition of claim 1, wherein the combination of non-woven chitosan-based fibers further comprise a rheological modifier in an amount between about 0% and about 10% (w/w).

22. The composition of claim 1, further comprising non-woven chitosan-based fibers that are not cross-linked.

23. The composition of claim 1, wherein the centrifugally spun non-woven chitosan-based fibers in the at least one of the layers consisting of a combination of (a) and (b) are cylindrical in shape.

24. The composition of claim 1, wherein the non-woven chitosan-based fibers have a positively charged surface.

* * * * *